US008790659B2

(12) United States Patent
Scholz et al.

(10) Patent No.: US 8,790,659 B2
(45) Date of Patent: Jul. 29, 2014

(54) SLPA AS A TOOL FOR RECOMBINANT PROTEIN AND ENZYME TECHNOLOGY

(75) Inventors: Christian Scholz, Penzberg (DE); Elke Faatz, Huglfing (DE); Urban Schmitt, Kochel (DE); Peter Schaarschmidt, Uffing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/569,353

(22) Filed: Aug. 8, 2012

(65) Prior Publication Data
US 2012/0308994 A1  Dec. 6, 2012

Related U.S. Application Data

(63) Continuation of application No. 12/436,396, filed on May 6, 2009, now Pat. No. 8,263,086.

(30) Foreign Application Priority Data

May 26, 2008 (EP) ..................................... 08009537

(51) Int. Cl.
*A61K 39/245* (2006.01)
(52) U.S. Cl.
USPC .......... 424/231.1; 424/204.1; 435/5; 530/300
(58) Field of Classification Search
None
See application file for complete search history.

(56) References Cited

U.S. PATENT DOCUMENTS 7,157,089 B1  1/2007  Mizzen et al.

FOREIGN PATENT DOCUMENTS

| EP | 1971684 | * 12/2006 | ................ C12N 9/90 |
|---|---|---|---|
| WO | 03/000878 A3 | 1/2003 | |
| WO | 2007/077008 A1 | 7/2007 | |

OTHER PUBLICATIONS

Schenk et al. Evaluation of a new ELISA for the detection of specific IgG to the Epstein-Barr nuclear antigen 1 (EBNA-1). Clin Lab. 2007;53(3-4):151-5. ABS only.*
Allday and MacGillivray. Epstein-Barr Nuclear Antigen (EBNA): Size polymorphisma of EBNA 1. J. Gen. Virol. 1985, 66: p. 1596-1600.*
Bouvier, J. and Stragier, P., "Nucleotide sequence of the lsp-dapB interval in *Escherichia coli*," Nucleic Acids Research, 1991, p. 180, vol. 19, No. 1.
Ghiasi, Homayon et al., "Baculovirus-Expressed Glycoprotein G of Herpes Simplex Virus Type 1 Partially Protects Vaccinated Mice against Lethal HSV-1 Challenge," Virology, 1992, pp. 233-239, vol. 190.
Han, Kyung-Yeon et al., "Solubilization of aggregation-prone heterologous proteins by covalent fusion of stress-responsive *Escherichia coli* protein, SlyD," Protein Engineering, Design & Selection, 2007, pp. 1-7.
Hottenrott, Sandra et al., "The *Escherichia coli* SlyD Is a Metal Ion-regulated Peptidyl-prolyl cis/trans-Isomorase," The Journal of Biological Chemistry, Jun. 20, 1997, pp. 15697-15701, vol. 272, No. 25.
Kakkanas, Athanassios et al., "*Escherichia coli* Expressed Herpes simplex Virus gG1 and gG2 Proteins in ELISA and Immunoblotting Assays," Interviology, Nov./Dec. 1995, pp. 346-351, vol. 38, No. 8.
Kwon, Soonbok et al., "Proteomic analysis of heat-stable proteins in *Escherichia coli*," BMB Reports, 2008, pp. 108-111, vol. 41, No. 2.
Scholz, Christian et al., "Chaperone-Aided in Vitro Renaturation of an Engineered E1 Envelope Protein for Detection of Anti-Rubella Virus IgG Antibodies," Biochemistry, 2008, pp. 4276-4287, vol. 47.
Scholz, Christian et al., "Functional Solubilization of Aggregation-prone HIV Envelope Proteins by Covalent Fusion with Chaperone Modules," Journal of Molecular Biology, 2005, pp. 1229-1241, vol. 345.
Suzuki, Rintaro et al., "Three-dimensional Solution Structure of an Archaeal FKBP with a Dual Function of Peptidyl Prolyl cis-trans Isomerase and Chaperone-like Activities," Journal of Molecular Biology, 2003, pp. 1149-1160, vol. 328.
Thapa, A. et al., "Purification of inclusion body-forming peptides and proteins in soluble form by fusion to *Escherichia coli* thermostable proteins," Biotechniques, May 2008, pp. 787-796, vol. 44, No. 6.
Zandi, Keivan et al., "Production of recombinant gG-1 protein of herpes simplex virus type 1 in a prokaryotic system in order to develop a type-specific enzyme-linked immunosorbent assay kit," FEMS Immunol Med Microbiol, 2007, pp. 319-323, vol. 50.
Scholz, Christian et al., "SlyD Proteins from Different Species Exhibit High Prolyl Isomerase and Chaperone Activities," Biochemistry, 2006, pp. 20-33, vol. 45.

* cited by examiner

*Primary Examiner* — Michelle S Horning
(74) *Attorney, Agent, or Firm* — Roche Diagnostics Operations, Inc.

(57) ABSTRACT

Disclosed are a recombinant DNA molecule encoding a fusion protein comprising a SlpA chaperone and a target polypeptide wherein human FK506 binding proteins (FKBPs) are excluded as target polypeptides, a corresponding expression vector encoding said fusion protein as well as host cells transformed with said expression vector. Also disclosed are a method for producing the fusion protein, a recombinantly produced fusion protein comprising a SlpA chaperone and a target polypeptide. A further aspect of the invention is the use of the recombinantly produced fusion protein, and a reagent kit containing a recombinantly produced fusion protein comprising a SlpA chaperone and a target polypeptide.

20 Claims, 9 Drawing Sheets

SLPA AS A TOOL FOR RECOMBINANT PROTEIN AND ENZYME TECHNOLOGY

RELATED APPLICATIONS

This application is a continuation of U.S. patent application Ser. No. 12/436,396 (U.S. Patent Publication No. 2009-0291892), filed May 6, 2009, which claims the benefit of European Patent Application No. 08009537.5, filed May 26, 2008, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Aug. 6, 2012, is named 24705_US1_SEQ_LISTING.txt, and is thirty-seven thousand eight hundred and ninety-four bytes in size.

FIELD OF THE INVENTION

The present invention relates to fusion proteins comprising a SlpA chaperone and a target polypeptide, methods of recombinantly expressing, purifying and refolding these fusion proteins, their uses in protein and enzyme biotechnology, and particularly their applications in diagnostics. Further, the invention relates to any complex comprising SlpA and a target polypeptide, which is intended to increase the solubility, the activity, the stability and/or the folding reversibility of the target polypeptide or enzyme for biotechnological applications.

BACKGROUND OF THE INVENTION

Protein folding is a spontaneous process that is driven by the small difference in Gibbs free energy between the native and unfolded state. Within the folding process, a largely unstructured polypeptide chain adopts what is termed the native conformation or three-dimensional structure of a protein. Aggregation of incompletely folded molecules competes with productive folding, and this constitutes a major problem and affects the folding yields both in vivo and in vitro. In living cells, folding is assisted by helper proteins. Folding helpers are polypeptides that assist the folding and maintain the structural integrity of other proteins. They possess the ability to promote the proper folding of a polypeptide chain by reversibly interacting with their target, thereby preventing detrimental side reactions such as aggregation processes. They do so both in vivo and in vitro, and there is an ever increasing number of applications of these folding helpers in biotechnological problems. Generally, folding helpers are subdivided into folding catalysts and chaperones.

Chaperones are known to reversibly bind to denatured, partially denatured or, put simply, hydrophobic surfaces of polypeptides and thus help to renature proteins or to keep them in solution. Chaperones lower the concentration of aggregation-prone folding intermediates and aggregation-prone folded proteins by reversibly binding and masking hydrophobic surfaces. They thus exert a mere binding function. In contrast, folding catalysts such as disulfide oxidoreductases and peptidyl-prolyl cis/trans isomerases accelerate rate limiting steps in protein folding and thus shorten the lifetime of folding intermediates. Folding catalysts thus lower the concentration of aggregation-prone folding intermediates due to their catalytic function. An important class of folding catalysts is referred to as peptidyl prolyl cis/trans isomerases (PPIases).

Based on sequence similarity, protein topology and binding of immunosuppressant molecules, prolyl isomerases are distinguished into three distinct families, the cyclophilins, the parvulins and the FK506 binding proteins (hence the acronym FKBPs). FKBPs bind to and are inhibited by FK506, rapamycin and related macrolide derivatives, which have been used as immunosuppressant drugs.

A putative folding helper that belongs to the FKBP family of peptidyl prolyl cis/trans isomerases in *E. coli* is SlpA, SlpA being the acronym for "SlyD-like protein A" (Hottenrott et al. 1997, JBC 272/25, 15697-15701). Up to now, information on SlpA and its physiological role in *E. coli* has been scarce. Although a poor prolyl isomerase activity of SlpA has been reported, this protein has hitherto remained rather enigmatic. So far, information on the physico-chemical or possible chaperone properties of SlpA has been lacking, and the function of SlpA in the *E. coli* cytosol has not even been addressed.

In many diagnostic applications recombinantly produced proteins are used as binding partners, e.g., as antigens in an immunoassay designed for the detection of a specific immunoglobulin analyte. These antigens may be produced as fusion proteins containing one part that makes up the target portion or antigenic polypeptide which is intended to recognize and bind a specific moiety present in the sample or in the assay mixture under study. The other part of the recombinantly produced fusion protein is a polypeptide portion that is fused to the specificity-conferring antigenic part in order to facilitate its cloning, expression, overproduction, folding/refolding and purification, and to increase its solubility, its stability or its reversibility of folding. The synthesis of recombinantly produced fusion proteins is well described in prior art. It is also well-established that it is advantageous to use chaperones as that part of the fusion protein that serves a role as a helping molecule for the expression, folding, purification, solubilization, and the increase in the overall stability of the target polypeptide.

U.S. Pat. No. 6,207,420 discloses a fusion protein system for the expression of proteins, in which the amino acid sequences of the target polypeptide part and the fused peptide part originate from different organisms. Recently it could be shown that FkpA and SlyD are suitable as fusion modules for the production of recombinant proteins. Both chaperones increase the expression rate of their client proteins in a prokaryotic host, support correct refolding and increase the overall solubility of even extremely aggregation-prone proteins such as retroviral transmembrane proteins (Scholz et al. 2005, JMB 345, 1229-1241 and WO 03/000877).

While FkpA and SlyD are particularly useful in helping difficult or aggregation-prone proteins to adopt and maintain their native structure in diagnostic reagents and, more generally speaking, biotechnological applications, there remains the challenge of thermal stability. The native conformation of proteins is stabilized by a carefully balanced network of van-der-Waals contacts, hydrogen bonds, salt bridges and hydrophobic interactions. These contacts are optimized for the microenvironment of the respective protein, and changes in pH, ionic strength or temperature do perturb and shift the equilibrium between folded and unfolded molecules. An increase in temperature is particularly well suited to denature proteins, which often results in aggregation of the fully or partially unfolded molecules. Thermally induced aggregation of proteins with the concomitant loss of function constitutes a major problem of any protein formulation. It is well conceivable that elevated temperatures, or, more generally speaking, thermal stress may occur during inappropriate shipment or storage of protein reagents or formulations.

A chaperone fusion module such as SlyD, for instance, shows an onset of thermally induced unfolding at a temperature around 42° C., a temperature which is easily exceeded, e.g., when the cooling system is defective in a container used for transportation, shipment or storage of a protein formulation. In case the target protein X is highly hydrophobic and fully depends on the chaperoning activity of its fusion partner, the complete fusion polypeptide will aggregate as soon as the SlyD module unfolds and concomitantly loses its solubilizing function. In other words, the stability of SlyD limits the overall stability of a SlyD-X fusion polypeptide when X is a very hydrophobic and aggregation-prone client protein.

Fusion proteins comprising FkpA show a slightly increased stability, probably due to the higher intrinsic thermostability of the dimeric FkpA carrier module. The melting temperature of E. coli SlyD has been determined at around 42° C., whereas FkpA is rather stable up to around 50° C. Yet, for reasons that are outlined in the following section, there remains the urgent need to provide alternative functional chaperone variants with high intrinsic stability.

In a heterogeneous immunoassay of the double antigen sandwich (DAGS) format, for instance, two variants of an antigen are employed on either side of the assay. One of these variants bears a label with a high affinity for the solid phase, the other bears a signaling moiety in order to generate a signal output. Each of these antigen variants may be fused to a helper sequence, i.e., a carrier or fusion module. At least one chaperone (or a functional polypeptide binding domain, i.e., a chaperone domain) is attached or fused to the target polypeptide and facilitates folding, increases stability and solubility and maintains the target polypeptide in a suitable conformation so that the antibody analyte to be determined can specifically recognize and bind the target polypeptide. Preferably, different chaperones are used as fusion partners on either side of an immunological bridge assay, in order to break the inherent symmetry of the assay. An assay format containing different carrier or fusion modules but identical or similar target polypeptides on either side (i.e., on the capture and the detection side) may also be termed an asymmetric DAGS format. By using different fusion modules on each side of a DAGS assay, the risk of immunological cross-reactions due to the carrier modules and, concomitantly, erroneously high signals may be substantially reduced.

Clearly, the overall stability of the assay is limited by the immunological component with the lowest inherent stability. When using FkpA and SlyD as fusion partners in an asymmetric DAGS, SlyD is the fusion partner that limits the overall stability. Thus, there is an obvious need to find other chaperones, which can fully replace SlyD functionally and which are inherently more stable towards thermal stress. Even though a wealth of SlyD homologues from thermophilic or hyperthermophilic organisms have been described, there is a caveat in simply using these proteins as fusion partners: Since they have been evolved and optimized for temperatures far beyond 60° C., they possess an extremely high thermodynamic stability. As a consequence, stable and hyperstable proteins often tend to become rather rigid at ambient temperature, i.e., they lose the flexibility which is a prerequisite for dynamic binding to target molecules. It is widely accepted that the stability of a protein can only be increased at the expense of both its flexibility and function, which often precludes highly stable proteins from applications at ambient temperature. An object of the present invention is therefore to identify thermostable folding helpers from mesophilic organisms. A further object of the present invention is to provide polypeptides suitable for diagnostic and biotechnological applications that possess an increased thermal stability and prolong the shelf life of diagnostic reagents and protein formulations.

A few proteins of E. coli are stable and soluble at temperatures far beyond 49° C. as reported recently by Kwon et al. (BMB reports 2008, 41(2), 108-111). The proteins that were soluble upon exposure to elevated temperature were identified by SDS polyacrylamide gel electrophoresis. The study was carried out with sonicated extracts of E. coli after incubation at various temperatures. Amongst the 17 heat-stable proteins that were identified, 6 proteins turned out to be putative folding helpers (GroEL, GroES, DnaK, FkpA, trigger factor, EF-Ts). It is noteworthy that the experiment was performed with a cell-free lysate of E. coli and that the solubility of the respective protein was taken as the sole criterion for stability.

There is, however, a substantial difference between the solubility and the stability of a protein. It is well known in the art that the solubility of a protein often reaches a minimum at conditions of maximal stability. For instance, the thermodynamic stability of a protein reaches a maximum when the pH of the buffer solution coincides with the pI of the respective protein. Yet, under these very conditions, the protein solubility reaches a minimum. Another popular example is the salting-out of proteins by means of ammonium sulfate or other cosmotropic agents: here also, the solubility of a protein decreases as its stability is increased (ammonium sulfate is a strongly cosmotropic agent, i.e., it stabilizes protein structures).

WO 2007/077008 discloses recombinantly produced chimeric fusion proteins that contain the polypeptide binding segment of a non-human chaperone like, e.g., E. coli SlyD, and N- and C-terminally fused thereto a human FKBP type peptidyl-prolyl-cis/trans isomerase. A similar fusion polypeptide has been disclosed using a chaperone segment of SlpA.

Surprisingly, SlpA, in particular E. coli SlpA, is able to confer thermal stability on other target polypeptides when used as a fusion partner. As reported by Hottenrott et al. (supra) SlpA is an enzyme with a rather poor peptidyl-prolyl cis/trans isomerase activity. Unexpectedly, SlpA exhibits also pronounced chaperone features and, even more surprisingly, SlpA possesses an high intrinsic stability and confers thermal stability on a fused target polypeptide thereby making the target polypeptide less susceptible to heat-induced aggregation. Whereas the closely related SlyD exhibits only a marginal stability with a midpoint of thermal unfolding at around 42° C., SlpA retains its native fold at least up to 50° C. and shows a midpoint of thermal unfolding (defined as the melting temperature) at around 56° C. This is indeed puzzling given the close relationship between SlyD and SlpA (which stands for SlyD-like protein) and given the fact that both are monomeric proteins from a mesophilic organism such as E. coli with a maximum growth temperature of 49° C. Most surprisingly, the mesophilic organism E. coli harbors a putative folding helper such as SlpA that combines outstanding thermostability and chaperone features.

SUMMARY OF THE INVENTION

The present invention relates to a recombinant DNA molecule encoding a fusion protein comprising a SlpA chaperone and a target polypeptide, a corresponding expression vector encoding said fusion protein as well as host cells transformed with said expression vector. Another aspect of the invention is a method for producing said fusion protein as well as a recombinantly produced fusion protein comprising a SlpA chaperone and a target polypeptide. A further aspect of the invention is the use of the recombinantly produced fusion protein as a binding partner (such as an antigen, an enzyme or a recombinant calibrator material) or as a means for the reduction of interferences in an immunoassay. Further the invention relates to the use of the recombinantly produced fusion protein as an immunogen for the production of antibodies against the target polypeptide and to the use of the recombinantly produced fusion protein in the production of a vaccine. Yet another aspect is a method for the detection of an analyte in an immunoassay using a recombinantly produced fusion protein as well as a reagent kit containing a recombinantly produced fusion protein comprising a SlpA chaperone and a target polypeptide. A further aspect concerns the use of SlpA as a means for the reduction of interferences and cross-reactions in immunoassays. Yet another aspect of the invention is the use of soluble and functional complexes comprising SlpA and a target protein intended for biotechnological applications, whereby the target protein may be of therapeutic or diagnostic value.

BRIEF DESCRIPTION OF THE FIGURES

FIG. 3 clearly illustrates the superior thermal stability of SlpA.

Figure 9:
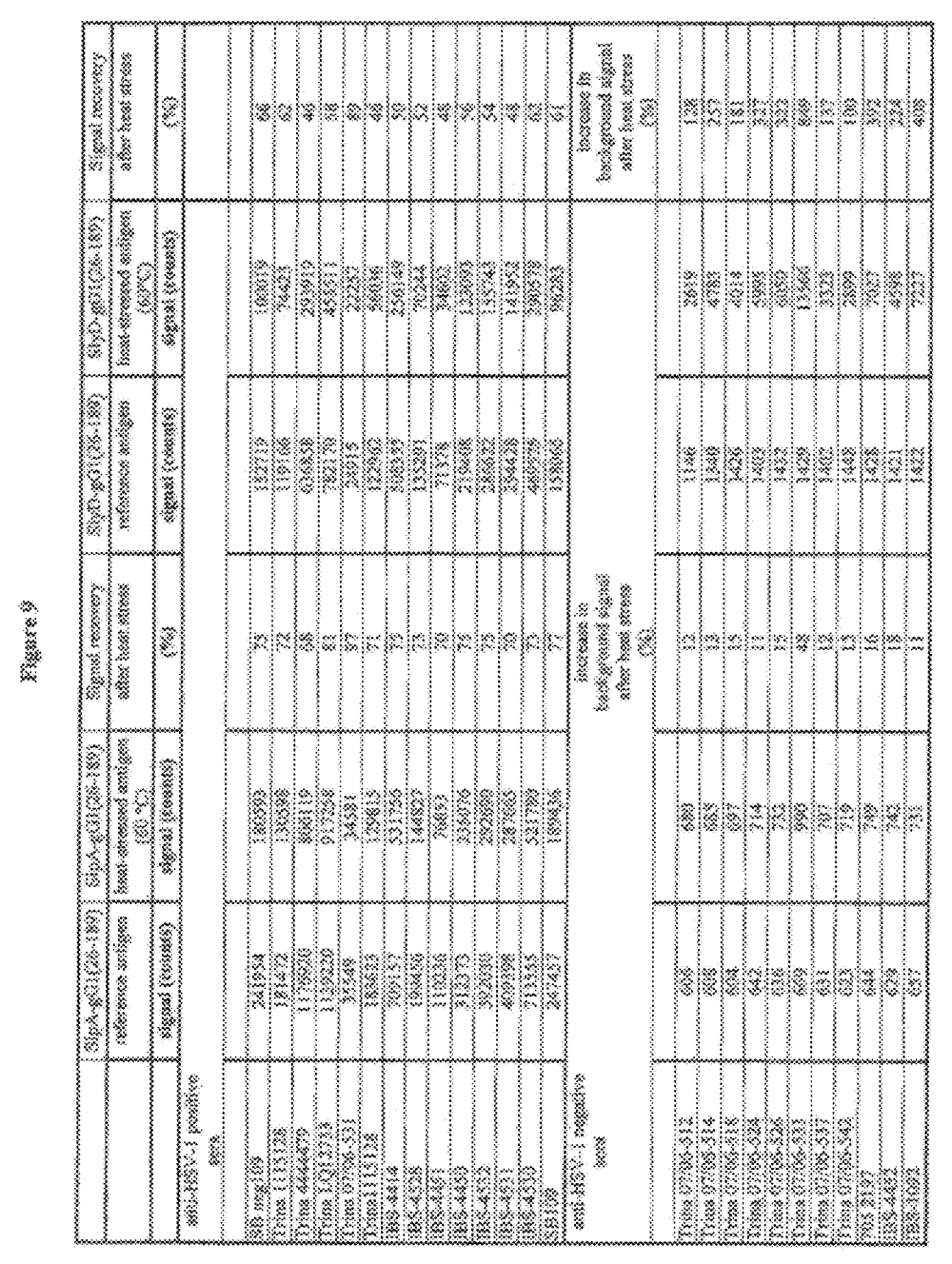

FIG. 9: Immunological reactivity of SlpA-gG1 (26-189) and SlyD-gG1 (26-189) with human anti-HSV-1 positive and anti-HSV-1 negative sera in an automated ELECSYS analyzer (Roche Diagnostics GmbH) as described in Example 4. Table 1 demonstrates the performance of both antigen variants before and after a harsh overnight heat-treatment at 60° C. The outcome of the experiments clearly shows the superiority of heat-stressed SlpA-gG1 (26-189) over heat-stressed SlyD-gG1 (26-189) in a twofold manner. Firstly, the signal recovery with anti-HSV-1 positive sera (upper half of Table 1) is significantly higher with the heat-stressed SlpA fusion polypeptide. Secondly, the increase in background signal with anti-HSV-1 negative sera (lower half of Table 1) is significantly lower with the heat-stressed SlpA fusion polypeptide. Both effects improve the signal dynamics of the immunoassay and highlight the advantages of SlpA as a stability- and solubility-conferring fusion partner for difficult target proteins. Thus, the sensitivity of an immunoassay can be warranted by using SlpA as a fusion partner instead of the closely related SlyD.

BRIEF DESCRIPTION OF THE SEQUENCE LISTING

Figure 1:
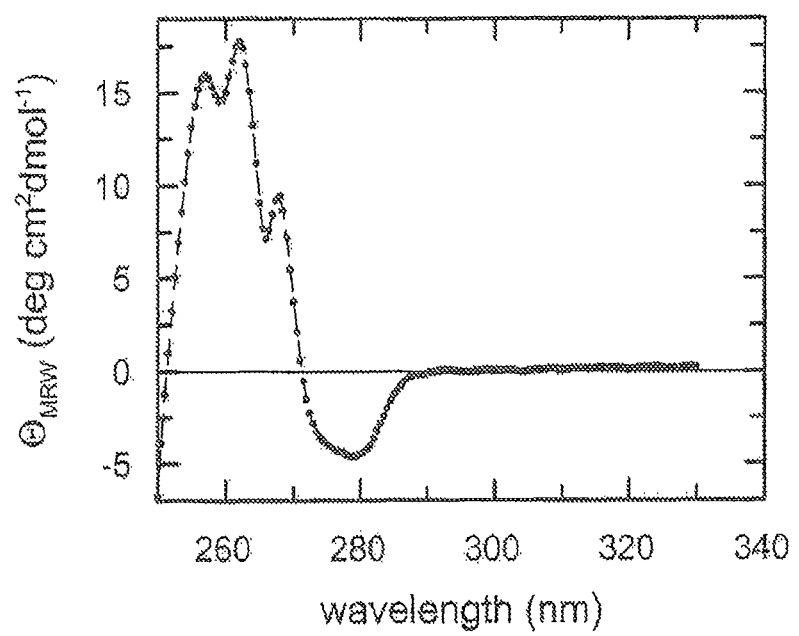
FIG. 1: Near-UV CD spectrum of SlpA from *E. coli*. The spectrum was recorded on a Jasco-720 spectropolarimeter in a thermostated cell holder at 20° C. The protein concentration was 417 µM in a 1 cm cuvette. The buffer was 50 mM potassium phosphate pH 7.5, 100 mM KCl, 1 mM EDTA. Band width was 2 nm, resolution was 0.5 nm, the scanning speed was 50 nm/min at a response of 2 s. Spectra were recorded 9 times and averaged in order to improve the signal-to-noise ratio. The signal was converted to mean residue ellipticity (given in deg cm$^2$ dmol$^{-1}$). The spectrum points to a native-like folded protein, the signal maximum is at 262 nm.
Figure 2:
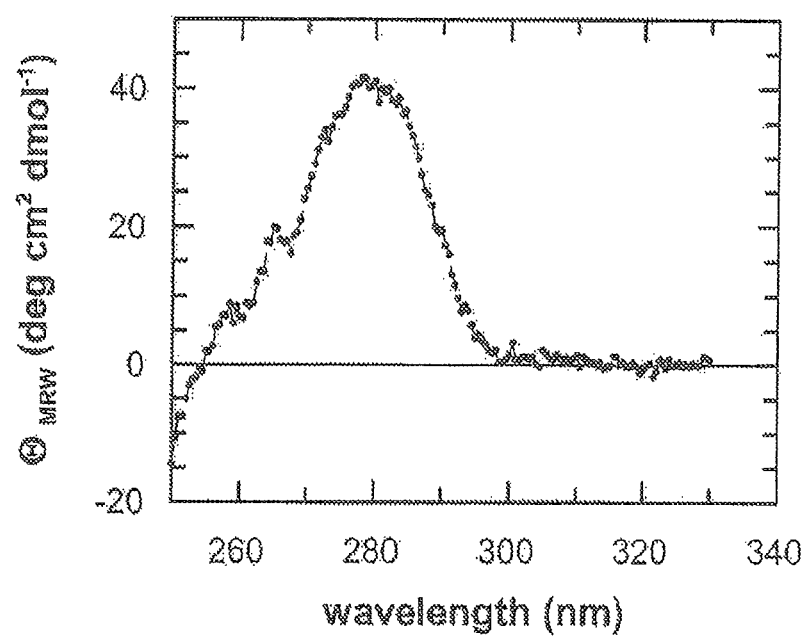
FIG. 2: Near-UV CD spectrum of SlyD from *E. coli*. The spectrum was recorded on a Jasco-720 spectropolarimeter in a thermostated cell holder at 20° C. The protein concentration was 200 µM in a 1 cm cuvette. The buffer was 50 mM potassium phosphate pH 7.5, 100 mM KCl, 1 mM EDTA. Band width was 2 nm, resolution was 0.5 nm, the scanning speed was 50 nm/min at a response of 1 s. Spectra were recorded 9 times and averaged in order to improve the signal-to-noise ratio. The signal was converted to mean residue ellipticity (given in deg cm$^2$ dmol$^{-1}$). The spectrum of SlyD significantly differs from the spectrum of SlpA. It points to a native-like folded protein, the signal maximum is at 275 nm.
Figure 3:
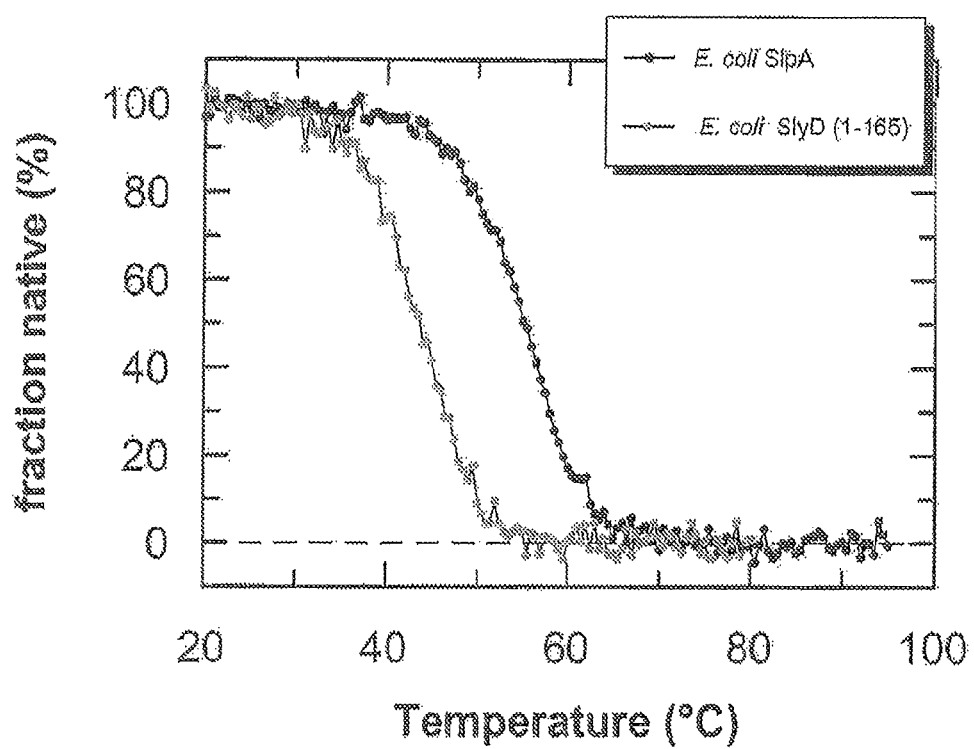
FIG. 3: Thermally induced unfolding transitions of SlyD and SlpA as monitored by near-UV CD at 275 nm (SlyD) and 262 nm (SlpA). The melting curves are normalized to the fraction of native molecules. Unfolding of both SlyD and SlpA is fully reversible, and the near-UV CD signal of the native molecules can be fully restored after the thermal transition when the sample is chilled to ambient temperature. The melting temperature (i.e., the temperature at which 50% of the molecules are folded and 50% are unfolded) is 42° C. for SlyD and 56° C. for SlpA.
Figure 4:
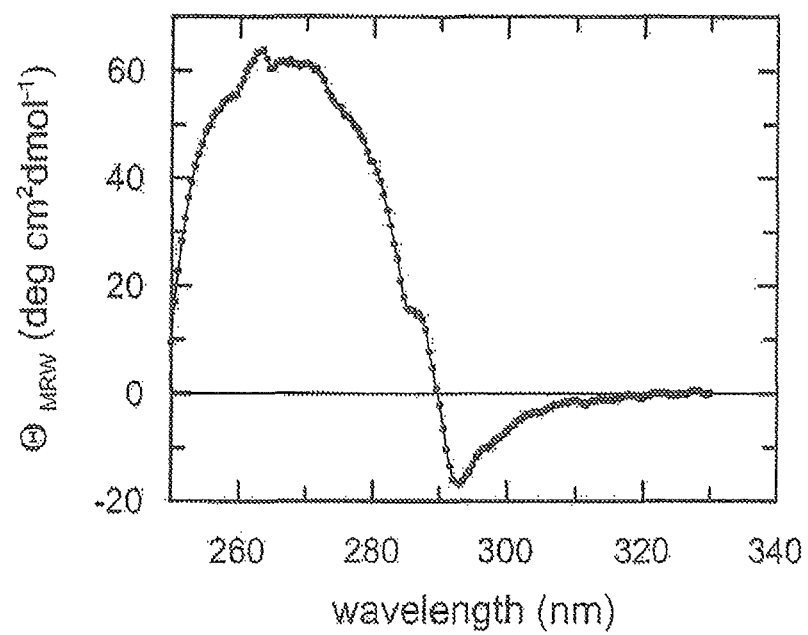
FIG. 4: Near-UV CD spectrum of the SlpA-gp41 fusion protein. The spectrum was recorded on a Jasco-720 spectropolarimeter in a thermostated cell holder at 20° C. The protein concentration was 18.7 µM in a 1 cm cuvette. The buffer was 50 mM potassium phosphate (pH 7.5), 100 mM KCl, 1 mM EDTA. Bandwidth was 2.0 nm, resolution was 0.5 nm, the scanning speed was 50 nm/min at a response of 2 s. Spectra were recorded 9 times and averaged in order to improve the signal-to-noise ratio. The signal was converted to mean residue ellipticity (given in deg cm$^2$ dmol$^{-1}$). The spectrum points to a native-like folded protein. The signal minimum at 293 is indicative of a native-like folded gp41 ectodomain fragment, which is rich in tryptophan residues and absorbs light beyond 280 nm. The signature around 290 nm unambiguously points to a native-like fold of the gp41 moiety within the SlpA-gp41 fusion polypeptide.
Figure 5:
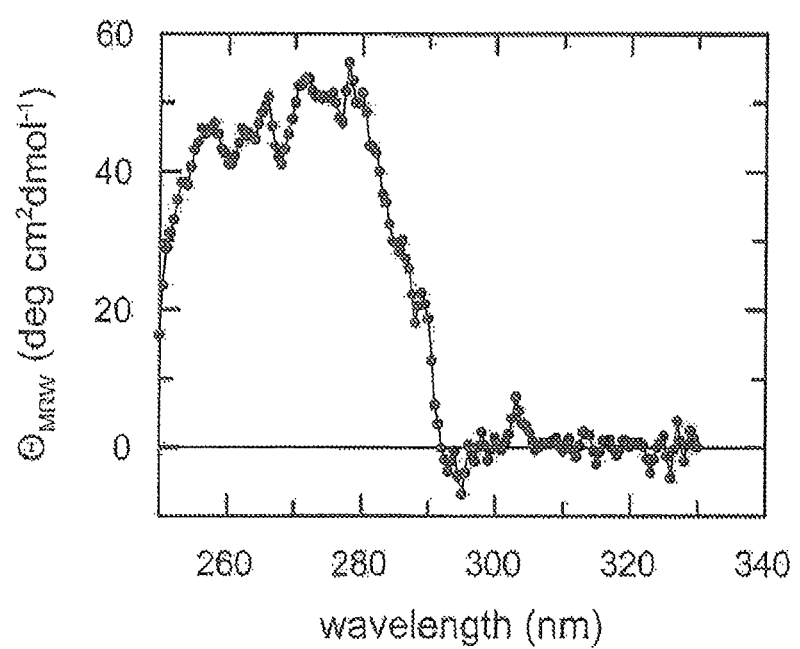
FIG. 5: Near-UV CD spectrum of the SlyD-gp41 fusion protein. The spectrum was recorded on a Jasco-720 spectropolarimeter in a thermostated cell holder at 20° C. The protein concentration was 14.4 µM in a 1 cm cuvette. The buffer was 50 mM potassium phosphate (pH 7.5), 100 mM KCl, 1 mM EDTA. Bandwidth was 2.0 nm, resolution was 0.5 nm, the scanning speed was 50 nm/min at a response of 2 s. Spectra were recorded 9 times and averaged in order to improve the signal-to-noise ratio. The signal was converted to mean residue ellipticity (given in deg cm$^2$ dmol$^{-1}$). The signal minimum at 293 is indicative of a native-like folded gp41 ectodomain fragment, which is rich in tryptophan residues and absorbs light beyond 280 nm. The signature around 290 nm strongly points to a native-like fold of the gp41 moiety within the SlyD-gp41 fusion polypeptide.
Figure 6:
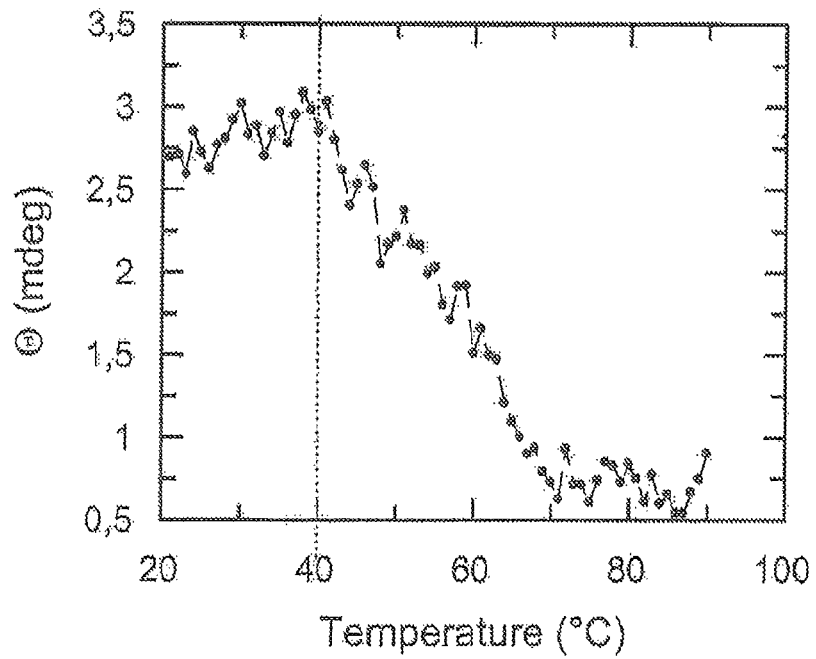
FIG. 6 A/B: The thermally induced unfolding of SlyD-gp41 (A) and SlpA-gp41 (B) is monitored via the decrease in the circular dichroic signal at 270 nm. Unfolding of the respective chaperone fusion partner goes along with the loss of its solubilization capacity and leads to spontaneous aggregation of the extremely hydrophobic gp41 moiety. The onset of aggregation is about 40° C. for SlyD-gp41 and about 56° C. for SlpA-gp41. The ellipticity is given in millidegrees (mdeg), the critical temperature boundaries beyond which (irreversible) aggregation occurs are highlighted by dashed lines.
Figure 6:
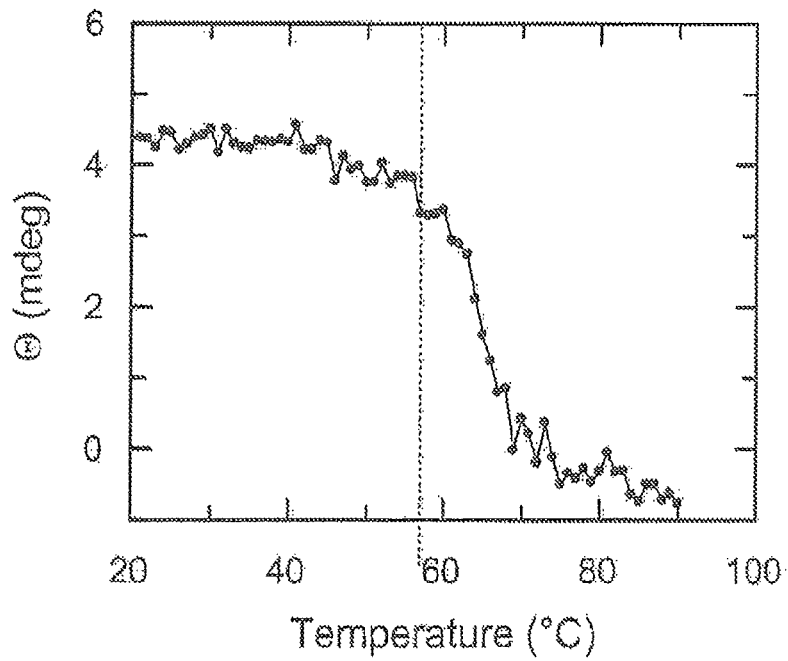

SEQ ID NO: 1 shows the complete amino acid sequence (149 amino acids) of *E. coli* SlpA, taken from the SwissProt database accession no. P0AEM0.

MSESVQSNSA VLVHFTLKLD DGTTAESTRN NGKPALFRLG DASLSEGLEQ HLLGLKVGDK TTFSLEPDAA

FGVPSPDLIQ YFSRREFMDA GEPEIGAIML FTAMDGSEMP GVIREINGDS ITVDFNHPLA GQTVHFDIEV

LEIDPALEA

SEQ ID NO: 2 shows the amino acid sequence of *E. coli* SlpA (amino acids serine 2 to glutamic acid 148) as used in the Examples section. The N-terminal methionine is removed cotranslationally in *E. coli*. To facilitate cloning the C-terminal alanine has been removed as well. Further, a C-terminal hexa-histidine tag (SEQ ID NO: 18) has been added to facilitate purification and refolding of the protein:

SESVQSNSAV LVHFTLKLDD GTTAESTRNN GKPALFRLGD ASLSEGLEQH LLGLKVGDKT TFSLEPDAAF

GVPSPDLIQY FSRREFMDAG EPEIGAIMLF TAMDGSEMPG VIREINGDSI TVDFNHPLAG QTVHFDIEVL

EIDPALEHHH HHH

SEQ ID NO: 3 shows the amino acid sequence of *E. coli* SlpA-gp41. The gp41 part contains amino acids 536-681 of HIV 1 gp41, the SlpA part contains amino acids 1-146. The sequence bears a C-terminal hexa-histidine tag (SEQ ID NO: 18) that has been added to facilitate the purification and the refolding of the fusion protein.

MSESVQSNSA VLVHFTLKLD DGTTAESTRN NGKPALFRLG

DASLSEGLEQ HLLGLKVGDK TTFSLEPDAA FGVPSPDLIQ

YFSRREFMDA GEPEIGAIML FTAMDGSEMP GVIREINGDS

ITVDFNHPLA GQTVHFDIEV LEIDPAGGGS GGGSGGGSGG

GSGGGSGGGT LTVQARQLLS GIVQQQNNEL RAIEAQQHLE

QLTVWGTKQL QARELAVERY LKDQQLLGIW GCSGKLICTT

AVPWNASWSN KSLEQIWNNM TWMEWDREIN NYTSLIHSLI

EESQNQQEKN EQELLELDKW ASLWNWFNIT NWLWYLEHHH HHH

SEQ ID NO: 4 shows the amino acid sequence of *E. coli* SlpA-SlpA-gp41. Two SlpA units are attached to the HIV gp41 ectodomain, which constitutes a strongly aggregation-prone target polypeptide. The first SlpA unit comprises amino acids 1-146, the second SlpA unit comprises amino acids 2-149 (both SlpA variants are fully equivalent in terms of function and stability). A C-terminal hexa-histidine tag (SEQ ID NO: 18) has been added to facilitate the purification and the refolding of the fusion protein.

MSESVQSNSA VLVHFTLKLD DGTTAESTRN NGKPALFRLG

DASLSEGLEQ HLLGLKVGDK TTFSLEPDAA FGVPSPDLIQ

YFSRREFMDA GEPEIGAIML FTAMDGSEMP GVIREINGDS

ITVDFNHPLA GQTVHFDIEV LEIDPAGGGS GGGSGGGSGG

GSGGGSGGGS ESVQSNSAVL VHFTLKLDDG TTAESTRNNG

KPALFRLGDA SLSEGLEQHL LGLKVGDKTT FSLEPDAAFG

VPSPDLIQYF SRREFMDAGE PEIGAIMLFT AMDGSEMPGV

IREINGDSIT VDFNHPLAGQ TVHFDIEVLE IDPALEAGGG

SGGGSGGGSG GGSGGGSGGG TLTVQARQLL SGIVQQQNNE

-continued

LRAIEAQQHL EQLTVWGTKQ LQARELAVER YLKDQQLLGI

WGCSGKLICT TAVPWNASWS NKSLEQIWNN MTWMEWDREI

NNYTSLIHSL IEESQNQQEK NEQELLELDK WASLWNWFNI

TNWLWYLEHH HHHH

SEQ ID NO: 5 shows the amino acid sequence of *E. coli* SlyD-gp41. A C-terminal hexa-histidine tag (SEQ ID NO: 18) has been added to facilitate the purification and the in vitro refolding of the protein.

MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGTL TVQARQLLSG

IVQQQNNELR AIEAQQHLEQ LTVWGTKQLQ ARELAVERYL

KDQQLLGIWG CSGKLICTTA VPWNASWSNK SLEQIWNNMT

WMEWDREINN YTSLIHSLIE ESQNQQEKNE QELLELDKWA

SLWNWFNITN WLWYLEHHHH HH

SEQ ID NO: 6 shows the amino acid sequence of *E. coli* SlyD-SlyD-gp41. Two SlyD units are fused to the target polypeptide gp41. A C-terminal hexa-histidine tag (SEQ ID NO: 18) has been added to facilitate purification and in vitro refolding of the protein.

MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGS

-continued

```
GGGSGGGSGG GSGGGTLTVQ ARQLLSGIVQ QQNNELRAIE

AQQHLEQLTV WGTKQLQARE LAVERYLKDQ QLLGIWGCSG

KLICTTAVPW NASWSNKSLE QIWNNMTWME WDREINNYTS

LIHSLIEESQ NQQEKNEQEL LELDKWASLW NWFNITNWLW

YHGHDHDHDH HHHHH
```

SEQ ID NO: 7 shows the amino acid sequence of fusion polypeptide SlpA-gG1. One SlpA unit is fused to the target polypeptide gG1, containing amino acids 26-189 of human herpes simplex virus HSV-1 antigen gG1 as used in Example 4.

```
MSESVQSNSA VLVHFTLKLD DGTTAESTRN NGKPALFRLG

DASLSEGLEQ HLLGLKVGDK TTFSLEPDAA FGVPSPDLIQ

YFSRREFMDA GEPEIGAIML FTAMDGSEMP GVIREINGDS

ITVDFNHPLA GQTVHFDIEV LEIDPALEGG GSGGGSGGGS

GGGSGGGSGG GPTNVSSTTQ PQLQTTGRPS HEAPNMTQTG

TTDSPTAISL TTPDHTPPMP SIGLEEEEEE EGAGDGEHLE

GGDGTRDTLP QSPGPAFPLA EDVEKDKPNR PVVPSPDPNN

SPARPETSRP KTPPTIIGPL ATRPTTRLTS KGRPLVPTPQ

HTPLFSFLTA SPALDLEHHH HHH
```

SEQ ID NO: 8 shows the amino acid sequence of fusion polypeptide SlyD-gG1. One SlyD unit is fused to the target polypeptide gG1, containing amino acids 26-189 of human herpes simplex virus HSV-1 antigen gG1 as used in Example 4.

```
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGPT NVSSTTQPQL

QTTGRPSHEA PNMTQTGTTD SPTAISLTTP DHTPPMPSIG

LEEEEEEEGA GDGEHLEGGD GTRDTLPQSP GPAFPLAEDV

EKDKPNRPVV PSPDPNNSPA RPETSRPKTP PTIIGPLATR

PTTRLTSKGR PLVPTPQHTP LFSFLTASPA LDLEHHHHHH
```

SEQ ID NO: 9 shows the amino acid sequence of *Pasteurella multocida* SlyD (full length) according to Swiss Prot ID: Q9CKP2

```
MKIAKNVVVS IAYQVRTEDG VLVDEAPVNQ PLEYLQGHNN

LVIGLENALE GKAVGDKFEV RVKPEEAYGE YNENMVQRVP

KDVFQGVDEL VVGMRFIADT DIGPLPVVIT EVAENDVVVD

GNHMLAGQEL LFSVEVVATR EATLEEIAHG HIHQEGGCCG

GHHHDSDEEG HGCGCGSHHH HEHEHHAHDG CCGNGGCKH
```

SEQ ID NO: 10 shows the amino acid sequence of the C-terminally truncated, cysteine-free *Pasteurella multocida* SlyD variant that is preferably used as a chaperone unit in a fusion protein for use in a double antigen sandwich immunoassay (PmS SlyD 1-156).

```
MKIAKNVVVS IAYQVRTEDG VLVDEAPVNQ PLEYLQGHNN

LVIGLENALE GKAVGDKFEV RVKPEEAYGE YNENMVQRVP

KDVFQGVDEL VVGMRFIADT DIGPLPVVIT EVAENDVVVD

GNHMLAGQEL LFSVEVVATR EATLEEIAHG HIHQEG
```

SEQ ID NO: 11 shows the amino acid sequence of *E. coli* FkpA (full-length) according to Swiss Prot ID P45523.

```
MKSLFKVTLL ATTMAVALHA PITFAAEAAK PATAADSKAA

FKNDDQKSAY ALGASLGRYM ENSLKEQEKL GIKLDKDQLI

AGVQDAFADK SKLSDQEIEQ TLQAFEARVK SSAQAKMEKD

AADNEAKGKE YREKFAKEKG VKTSSTGLVY QVVEAGKGEA

PKDSDTVVVN YKGTLIDGKE FDNSYTRGEP LSFRLDGVIP

GWTEGLKNIK KGGKIKLVIP PELAYGKAGV PGIPPNSTLV

FDVELLDVKP APKADAKPEA DAKAADSAKK
```

SEQ ID NO: 12 shows the amino acid sequence part of *E. coli* FkpA that is preferably used as a chaperone unit in a fusion protein for use in a double antigen sandwich immunoassay. The sequence is lacking the N-terminal signal sequence (amino acid residues 1-25) and essentially corresponds to the mature FkpA (FkpA 26-270)

```
AEAAKPATAA DSKAAFKNDD QKSAYALGAS LGRYMENSLK

EQEKLGIKLD KDQLIAGVQD AFADKSKLSD QEIEQTLQAF

EARVKSSAQA KMEKDAADNE AKGKEYREKF AKEKGVKTSS

TGLVYQVVEA GKGEAPKDSD TVVVNYKGTL IDGKEFDNSY

TRGEPLSFRL DGVIPGWTEG LKNIKKGGKI KLVIPPELAY

GKAGVPGIPP NSTLVFDVEL LDVKPAPKAD AKPEADAKAA DSAKK
```

SEQ ID NO: 13 shows the amino acid sequence of Epstein-Ban Virus nuclear antigen 1 (EBV nuclear antigen 1 or EBNA-1) from position 401-641, (EBV=HHV-4=human herpes virus 4); strain B95-8.

The complete amino acid sequence of EBNA-1 consists of 641 residues and is accessible under Swiss Prot ID P03211. The naturally occurring cysteine residues are dispensable for the antigenicity of EBNA-1 and have been changed to alanine (underlined) in order to simplify the purification process and to increase the yield of native-like folded soluble protein.

```
GRRPFFHPVG EADYFEYHQE GGPDGEPDVP PGAIEQGPAD

DPGEGPSTGP RGQGDGGRRK KGGWFGKHRG QGGSNPKFEN

IAEGLRALLA RSHVERTTDE GTWVAGVFVY GGSKTSLYNL

RRGTALAIPQ ARLTPLSRLP FGMAPGPGPQ PGPLRESIVA

YFMVFLQTHI FAEVLKDAIK DLVMTKPAPT ANIRVTVASF

DDGVDLPPWF PPMVEGAAAE GDDGDDGDEG GDGDEGEEGQ E
```

SEQ ID NO: 14 shows the amino acid sequence of Epstein-Ban Virus protein p18, amino acids 1 to 176 (open reading frame BFRF3, HHV-4/B95-8), according to Swiss Prot ID P14348. The naturally occurring cysteine residue at amino acid position 56 is dispensable for the antigenicity of EBV p18 and has been changed to alanine (underlined) in order to simplify the purification process and to increase the yield of native-like folded soluble protein.

```
MARRLPKPTL QGRLEADFPD SPLLPKFQEL NQNNLPNDVF

REAQRSYLVF LTSQFAYEEY VQRTFGVPRR QRAIDKRQRA

SVAGAGAHAH LGGSSATPVQ QAQAAASAGT GALASSAPST

AVAQSATPSV SSSISSLRAA TSGATAAASA AAAVDTGSGG

GGQPHDTAPR GARKKQ
```

SEQ ID NO: 15 shows the amino acid sequence of the C-terminal part of Epstein-Barr Virus protein p18, amino acids 105 to 176 (open reading frame BFRF3, HHV-4/B95-8), according to Swiss Prot ID P14348.

```
AASAGTGALA SSAPSTAVAQ SATPSVSSSI SSLRAATSGA

TAAASAAAAV DTGSGGGGQP HDTAPRGARK KQ
```

SEQ ID NO: 16 shows the amino acid sequence of Epstein-Ban Virus protein p23, amino acids 1 to 162 (open reading frame BLRF2, HHV-4/B95-8), according to Swiss Prot ID P03197. The naturally occurring cysteine residue at amino acid position 46 is dispensable for the antigenicity of EBV p23 and has been changed to alanine (underlined) in order to simplify the purification process and to increase the yield of native-like folded soluble protein.

```
MSAPRKVRLP SVKAVDMSME DMAARLARLE SENKALKQQV

LRGGAAASST SVPSAPVPPP EPLTARQREV MITQATGRLA

SQAMKKIEDK VRKSVDGVTT RNEMENILQN LTLRIQVSML

GAKGQPSPGE GTRPRESNDP NATRRARSRS RGREAKKVQI SD
```

SEQ ID NO: 17 shows the glycine-rich linker peptide sequence L=(GGGS)₅GGG as used and shown in example 1 for cloning of the expression cassettes comprising SlpA and a target polypeptide.

```
GGGSGGGSGG GSGGGSGGGS GGG
```

DETAILED DESCRIPTION OF THE INVENTION

An aspect of the current invention is a recombinant DNA molecule, encoding a fusion protein, comprising operably linked at least one nucleotide sequence coding for a target polypeptide and upstream or downstream thereto at least one nucleotide sequence coding for a SlpA chaperone unit.

The term "recombinant DNA molecule" refers to a DNA molecule which is made by the combination of two otherwise separated segments of sequence accomplished by the artificial manipulation of isolated segments of polynucleotides by genetic engineering techniques or by chemical synthesis. In doing so one may join together polynucleotide segments of desired functions to generate a desired combination of functions.

Polynucleotide sequences are operably linked when they are placed into a functional relationship with each other. For instance, a promoter is operably linked to a coding sequence if the promoter controls transcription or expression of the coding sequence. Generally, operably linked means that the linked sequences are contiguous and, where necessary to join two protein coding regions, both contiguous and in reading frame. However, it is well known that certain genetic elements, such as enhancers, may be operably linked even at a distance, i.e., even if not contiguous.

The terms "upstream" and "downstream" are functionally defined and refer to the direction or polarity of an encoding nucleotide sequence strand. "Upstream" direction means that the nucleotide is located in 5' direction of a given polynucleotide sequence, i.e., towards the starting nucleotide. In terms of amino acid sequence the term "upstream" translates into/means an amino acid that is located in N-terminal direction, i.e., towards the start of the polypeptide chain. Preferably, the nucleotide sequence encoding a SlpA chaperone unit is located upstream of the nucleotide sequence encoding the target polypeptide.

"Downstream" direction means that the nucleotide is located in 3' direction of the polynucleotide, i.e., towards the end of the nucleotide sequence. In terms of amino acid sequence the term "downstream" translated into an amino acid that is located in C-terminal direction, i.e., towards the end of the polypeptide chain.

A polynucleotide is said to "code for" or to "encode" a polypeptide if, in its native state or when manipulated by methods known in the art, the polynucleotide can be transcribed into a nucleotide template and/or be translated to yield the polypeptide or a fragment thereof.

Another aspect of the invention is an expression vector comprising operably linked a recombinant DNA molecule comprising at least one nucleotide sequence coding for a target polypeptide and upstream or downstream thereto at least one nucleotide sequence coding for a SlpA chaperone.

DNA constructs prepared for introduction into a host typically comprise a replication system recognized by the host, including the intended DNA fragment encoding the desired target fusion peptide, and will preferably also include transcription and translational initiation regulatory sequences operably linked to the polypeptide encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences.

The appropriate promoter and other necessary vector sequences are selected so as to be functional in the host. Many useful vectors for expression in bacteria, yeast, mammalian, insect, plant or other cells are known in the art and are commercially available. In addition, the construct may be joined to an amplifiable gene so that multiple copies of the gene may be obtained.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g., ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The vectors containing the polynucleotides of interest can be introduced into the host cell by any method known in the art. These methods vary depending on the type of the respective host system, including but not limited to transfection employing calcium chloride, rubidium chloride, calcium phosphate, DEAE-dextran, other substances, and infection by viruses. Large quantities of the polynucleotides and polypeptides of the present invention may be prepared by expressing the polynucleotides of the present invention in vectors or other expression vehicles in compatible host cells. The most commonly used prokaryotic hosts are strains of *Escherichia coli*, although other prokaryotes, such as *Bacillus subtilis* may also be used.

Expression in *Escherichia coli* represents a preferred mode of carrying out the present invention. Expression of fusion proteins comprising at least one SlpA unit and at least one target polypeptide X unit or coexpression of SlpA and X to yield soluble SlpA-X complexes, whether SlpA and X be covalently linked or not, is feasible in prokaryotic as well as in eukaryotic host cells.

Construction of a vector according to the present invention employs conventional ligation techniques. Isolated plasmids or DNA fragments are cleaved, tailored, and relegated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

A further embodiment of the invention is a host cell transformed with an expression vector comprising operably linked a recombinant DNA molecule comprising at least one nucleotide sequence coding for a target polypeptide and upstream or downstream thereto at least one nucleotide sequence coding for a SlpA chaperone.

Another embodiment of the invention refers to a method of coexpression of SlpA and a target polypeptide in a prokaryotic or eukaryotic host, whereby the overproduced SlpA interacts with the target polypeptide and forms a soluble non-covalent complex, which facilitates the preparation of native-like folded and active target polypeptide. This means that the DNA sequences encoding SlpA and the target polypeptide may be located on the same vector and controlled by either identical or different promoters. Alternatively, the DNA molecules encoding SlpA and the target polypeptide may be located on different compatible vectors. For simultaneous expression of SlpA and the target polypeptide host cells are transformed with both vectors. Preferably, the genes encoding the target protein and SlpA are controlled by different promoters, which are responsive to different inducers. Thus, induction of SlpA and target protein may be carried out simultaneously or consecutively in a controlled and defined manner. For instance, SlpA expression may be induced first to generate a basal level of functional chaperone, and subsequently the induction of the target gene may be carried out. This sequential approach aside, simultaneous induction of folding helper and target polypeptide is feasible and may yield soluble and functional target protein as well. The genes encoding SlpA and the target protein may be located on the same or on different vectors.

The term "fusion protein" means that two otherwise separated polypeptides are functionally combined on a single polypeptide chain. The single elements of the fusion protein, i.e., the SlpA chaperone part and the target polypeptide part, also termed target polypeptide X, may be directly adjacent to each other. Optionally they are separated by a peptide linker of 1-100 amino acid residues, preferably 5-30 amino acid residues, most preferably around 20 amino acid residues. As the skilled artisan will appreciate such a linker polypeptide is designed as most appropriate for the intended application, especially with regard to length, flexibility, charge and hydrophilicity. The linker polypeptide sequence may also contain a proteolytic cleavage site. Optionally the fusion protein may also contain a signal peptide sequence for targeting the protein to the desired compartment in which folding should take place.

According to the invention more than one target polypeptide X, e.g., two, three or four copies of the target polypeptide may be part of the fusion protein. As an example, SlpA-X2 means that one SlpA unit is fused to two target polypeptide units of the X type. The single target polypeptide units may or may not be separated by a linker polypeptide segment. The fusion protein contains at least one SlpA chaperone unit. As well, tandem, triple or higher combinations may constitute the fusion protein, e.g., SlpA-SlpA-X or SlpA-SlpA-SlpA-X. As well, fusion proteins in which the target polypeptide is sandwiched between at least two chaperone units, are part of the invention, e.g., SlpA-X-SlpA or SlpA-SlpA-X-SlpA-SlpA.

SlpA is a putative peptidyl prolyl cis/trans isomerase of the FKBP family. The *E. coli* SlpA amino acid sequence as published under SwissProt accession no. P0AEM0 is shown in SEQ ID NO: 1.

According to the invention the term "nucleotide sequence coding for a SlpA chaperone" refers to a nucleotide sequence encoding a polypeptide fragment comprising the polypeptide binding segment of SlpA. The term "polypeptide binding segment" of a chaperone denotes the binding-competent part of the chaperone, i.e., the part that binds and holds the client or substrate polypeptide chain and thus sequesters it to decrease the concentration of aggregation-prone folding intermediates and to facilitate subsequent folding. The "polypeptide binding segment" of SlpA may also be named IF domain (insert in flap domain). Defined as an autonomous folding unit, a protein domain is able to adopt a native-like stable fold in aqueous solution under appropriate refolding conditions. The terms "polypeptide binding segment", "IF-loop", IF-domain or chaperone domain may be used synonymously.

"SlpA" or "SlpA chaperone" or "SlpA unit" according to the invention comprises the polypeptide binding segment or IF domain of SlpA. Preferably, the entire molecule of *E. coli* SlpA is used as a fusion partner. Alternatively, the SlpA IF domain may be used as a fusion partner. It comprises at least a fragment N-terminally starting with any amino acid located between amino acid no. 59 and 78 of SEQ ID NO: 2 and C-terminally ending with any amino acid located between amino acid no. 125 and 139 of SEQ ID NO: 2. Most preferred is a sequence coding for a polypeptide N-terminally starting with amino acid no. 72 (Valine 72) and C-terminally ending with amino acid no. 132 (Threonine 132) of SEQ ID NO: 2. According to the invention, SlpA refers to the mature non-humanized form of this chaperone. This means that the SlpA chaperone does neither contain N- nor C-terminally flanking sequences of FKBP12 or any other human FKBP.

According to the invention, SlpA chaperone homologues from other organisms may be used as folding helpers combining a prolyl isomerase with a chaperone activity. Such SlpA homologues may originate from the following organisms (Swiss Prot database ID numbers are denoted in brackets): *Shigella flexneri* (Prot.ID. P0AEM3), *Shigella sonnei* (Prot.ID Q3Z5Y2), *Shigella dysenteriae* (Prot. ID Q32K69), *Citrobacter Koseri* (Prot.ID A8ALT4), *Salmonella typhi* (Prot.IDQ8XG79), *Salmonella typhimurium* (Prot.ID Q7CR92), *Salmonella paratyphi* A and B (Prot.ID Q5PKI5 and A9MYG7), *Salmonella choleraesuis* (Prot.ID Q57TL3), *Klebsiella pneumoniae* (Q9RF46), *Salmonella arizonae* (Prot.ID A9MR44), *Enterobacter* sp. (Prot.ID A4W6E3), *Enterobacter sakazakii* (A7MIM1), *Serratia proteamaculans* (Prot.ID A8G9L6), *Yersinia pestis* (Prot.ID Q8CZP4 or Q0WJI9), *Yersinia pseudotuberculosis* (Prot.ID A7FMD5), *Yersinia enterolitica* (A1JJE3), *Erwinia carotovora* (Prot.ID Q6D0C5), *Photorabdus luminescens* (Prot.ID Q7N8×0), *Sodalis glossinidius* (Prot.ID Q2NVY4), *Idiomarina baltica* (Prot.ID A3WMS1), *Vibrio harveyi* (Prot.ID A6ATG3 or A7MTD8), *Vibrio vulnificus* (Prot.ID Q7MNM6 or Q8DES9), *Vibrio campbellii* (Prot.ID A8T7R0), *Vibrio shilonii* (Prot.ID A6D8Q3), *Vibrio splendidus* (Prot.ID A3UXQ8), *Idiomarina loihiensis* (Prot.ID Q5QZR6), *Vibrio alginolyticus* (Prot.ID Q1V5T9), *Aeromonas salmonicida* (Prot.ID A4SIX7), *Photobacterium* sp. (Q2C7V1), *Vibrio parahaemolyticus* (Prot.ID Q87S88 or A6B565), *Pseudoalteromonas atlantica* (Prot.ID Q15R06), *Vibrio cholerae* (Prot.ID A5F8×4, or Q9KU45, or A6Y5H7, or A6XZU4, or A6ADB4, or A6A5W5, or A3H4C9, or A3 GPA9, or A3EG01, or A2PSS5, or A2P8T9, or A1F6Q8), *Aeromonas hydrophila* (Prot.ID A0KG41), *Vibrio angustum* (Prot.ID Q1ZMQ4), *Moritella* sp. (Prot.ID A6FG75), *Pseudoalteromonas haloplanktis* (Prot.ID Q31EA0), *Alteromonadales bacterium* (Prot.ID A0Y1B2), *Psychromonas ingrahamii* (Prot.ID A1SZP1), *Vibrio fischeri* (Prot.ID Q5E7N2 or A91PH0), *Photobacterium profundum* (Prot.ID Q1Z378 or Q6LUK9), *Pseudoalteromonas tunicata* (Prot.ID A4C627), *Psychromonas* sp. (Prot.ID Q1ZHS3), *Reineka* sp. (Prot.ID A4BJL0), *Vibrio psychroerythus* (Prot.ID Q486T8), *Shewanella amazonensis* (Prot.ID A15427), *Shewanella* sp. (Prot.ID Q0HFZ1, or Q0HS84, or A0KZY9), *Shewanella pealeana* (Prot.ID A8H1H5), *Shewanella frigidimarina* (Prot.ID Q07Z37), *Shewanella denitrificans* (Prot.ID Q12KM6), *Shewanella loihica* (Prot.ID A3QBX4), and *Shewanella putrefaciens* (Prot.ID A4Y4A6).

According to the invention the SlpA chaperone sequence may be modified by amino acid substitutions, preferably homologous substitutions, deletions and insertions provided that the overall structure, function and stability of the SlpA chaperone is maintained. Maintenance of the function of such a SlpA variant may easily be tested by determining the melting temperature of a fusion protein comprising a target polypeptide and the SlpA chaperone sequence under investigation. The melting temperature is defined as the temperature at which 50% of the molecules are folded and 50% are unfolded, i.e., the melting temperature determines the midpoint of the thermally induced unfolding transition in a given buffer system at a given protein concentration. Depending on the content in aromatic residues, the melting of proteins can be monitored by simple spectroscopic probes such as UV absorbance, fluorescence or circular dichroism. Circular dichroism, in particular, is well-suited to monitor conformational changes in the secondary structure (amide CD or far-UV CD) or in the tertiary structure (aromatic CD or near-UV CD) of proteins.

Thermally induced unfolding of SlpA as assessed by near-UV CD reveals that the unfolding process is fully reversible, i.e., SlpA spontaneously re-adopts its native conformation after the sample is chilled down from 95° C. to ambient temperature, i.e., to 15-25° C. This reversibility of folding and unfolding is a pivotal prerequisite for an ideal folding helper in biotechnological applications: Often, recombinant fusion proteins accumulate as inclusion bodies in the *E. coli* cytosol when they are heavily overproduced. In this case, a robust and efficient renaturation protocol has to be elaborated, starting off with bacterial cells or inclusion bodies lysed in 7.0 M guanidinium chloride or other chaotropic agents such as urea. It is self-evident that the refolding of any chaperone fusion partner must be sufficiently robust, efficient and reversible in order to assist the in vitro refolding of the desired client protein. Many fusion partners known in prior art such as, e.g., NusA, MBP (maltose binding protein) and GST (glutathione-S-transferase), exhibit a very robust de novo folding upon translation in the host cell, but they can not easily be refolded after thermally or chemically induced unfolding. These fusion partners are therefore employed with the aim of soluble expression of the target protein in the host system. When they fail to confer solubility on their client proteins during de novo folding upon translation in the host cell, recovery of the aggregated fusion proteins by in vitro renaturation attempts is difficult. According to the present invention, a fully reversible fusion partner such as SlpA has its obvious advantages in that it may as well lead to a soluble protein production upon de novo folding in the host cell. In addition, SlpA, by virtue of its folding reversibility, may as well be used to assist the in vitro refolding of a fusion polypeptide that has accumulated in insoluble inclusion bodies upon massive overproduction in the host cell. Complete reversibility of unfolding in combination with a high intrinsic stability and substantial chaperone features are important prerequisites of a fusion partner according to the present invention. These criteria are perfectly met by SlpA.

According to the invention, one or more, preferably two nucleotide sequences encoding a SlpA chaperone are located upstream of the nucleotide sequence coding for a target polypeptide, resulting in a tandem SlpA chaperone comprising two adjacent SlpA units. The one or more nucleotide sequences encoding a SlpA chaperone may be separated by a nucleotide sequence encoding (in frame) a peptide linker of 1-100 amino acids. Different nucleotide sequences may be used to encode the two SlpA chaperone units. As well, different nucleotide sequences should be used to encode all the other highly repetitive elements such as linker or spacer segments within the fusion polypeptide. The nucleotide sequences should be degenerated in order to avoid the loss of one SlpA coding sequence due to inadvertent recombination events in the *E. coli* host. By carefully selecting different codons for identical or repetitive amino acid sequences, the stability of the expression cassette can be secured.

A "target polypeptide" according to the invention may be any polypeptide (i.e., any amino acid sequence) that is limited in solubility or stability, that tends to aggregate under unfavorable conditions and that needs to be supported or assisted by a folding helper with the proviso that FK506 binding proteins (FKBPs), in particular human FK506 binding proteins, are excluded as target polypeptides. This means that FK506 binding proteins such as, e.g., human FKBP12 are excluded as target polypeptides. In a preferred embodiment, polypeptides that show a tendency to aggregate and/or are susceptible to thermal stress may be used as a target polypeptide. Moreover, polypeptides with enzymatic activity are preferred target polypeptides according to the invention. In particular, enzymes that accept and turn over hydrophobic substrates (and therefore harbor hydrophobic surface patterns themselves) are preferred target polypeptides according to the invention. In a further preferred embodiment, bacterial or viral proteins or prion proteins or proteins associated with rheumatoid arthritis are used as target polypeptides.

Any structural, membrane-associated, membrane-bound or secreted gene product of a mammalian pathogen may be used as a target polypeptide. Mammalian pathogens include viruses, bacteria, single-cell or multi-cell parasites which can infect or inhabit a mammalian host. For example, polypeptides originating from viruses such as human immunodeficiency virus (HIV), vaccinia, poliovirus, adenovirus, influenza, hepatitis A, hepatitis B, dengue virus, Japanese B encephalitis, Varicella zoster, cytomegalovirus, Epstein-Barr virus, rotavirus, as well as viruses causing measles, yellow fever, mumps, rabies, herpes, influenza, parainfluenza and the like may be used as a target polypeptide in the fusion protein according to the invention. Bacterial proteins of, e.g., *Vibrio cholerae, Salmonella typhi, Treponema pallidum, Helicobacter pylori, Bordetella pertussis, Streptococcus pneumoniae, Haemophilus influenzae, Clostridium tetani, Corynebacterium diphtheriae, Mycobacterium leprae, R. rickettsii, Shigella, Neisseria gonorrhoeae, Neisseria meningitidis, Coccidioides immitis, Borrelia burgdorferi*, and the like may be used as a target polypeptide.

Further examples of target polypeptides preferably produced by the present methods include mammalian gene products such as enzymes, cytokines, growth factors, hormones, vaccines, antibodies and the like. More particularly, preferred over expressed gene products of the present invention include gene products such as erythropoietin, insulin, somatotropin, growth hormone releasing factor, platelet derived growth factor, epidermal growth factor, transforming growth factor α, transforming growth factor, epidermal growth factor, fibroblast growth factor, nerve growth factor, insulin-like growth factor I, insulin-like growth factor II, clotting Factor VIII, superoxide dismutase, interferon, γ-interferon, interleukin-1, interleukin-2, interleukin-3, interleukin-4, interleukin-6, granulocyte colony stimulating factor, multi-lineage colony stimulating factor, granulocyte-macrophage stimulating factor, macrophage colony stimulating factor, T cell growth factor, lymphotoxin and the like. Preferred over expressed gene products are human gene products.

For diagnostic purposes, when, e.g., the analyte to be determined is an antibody, the target polypeptides contain at least one epitope that is recognized by the antibodies to be determined. Such epitopes are also called diagnostically relevant epitopes. A target polypeptide according to the invention may also comprise sequences like, e.g., diagnostically relevant epitopes from several different proteins constructed to be expressed as a single recombinant polypeptide. Preferably, the target polypeptide has a length of 10-500 amino acids.

Most preferably, the target polypeptide is a member of a group consisting of retroviral proteins such as gp41 and p17 from HIV-1, gp36 and p16 from HIV-2, gp21 from HTLV-I/II, consisting of viral envelope proteins such as E1 and E2 from Rubella virus or consisting of amyloidogenic proteins such as β-AP42 (Alzheimer peptide) or prion protein.

Also preferred as target polypeptides are the glycoprotein G1 from herpes simplex virus 1 and the glycoprotein G2 from herpes simplex virus 2. More exactly, the respective glycoprotein fragments lacking their signal sequences and their transmembrane regions (gG1 26-189, gG2 343-594) are suitable target polypeptides.

Further preferred as target polypeptides are the following proteins and protein fragments from Human Cytomegalovirus: pp28 (15-179), pp150 (821-1048), pp150 (547-725), pp150 (495-854), p38 (105-308), p38 (105-373), p38 (209-308), p52 (254-293), p52 (295-330), p52 (298-433), gB (67-84), pp65 (372-549), and pp65 (372-458).

Also preferred are the following proteins and protein fragments from *Treponema pallidum*: TpN17 (23-156), TpN47 (21-434), TpN15 (23-142), TmpA (23-345), TpO453 (27-287). The signal sequences of all these *Treponema* antigens have been omitted to ensure cytosolic localization upon expression in the *E. coli* host.

Further preferred target polypeptides are the following proteins and protein fragments from *Borrelia*: internal flagellin fragment p4 µl (137-262), VlsE (IR6/C6), DbpA (26-175), OspB (17-296), and OspC (19-214).

Further preferred target polypeptides are proteins from Epstein-Barr virus (EBV) such as EBV nuclear antigen 1 (EBNA-1) as shown in SEQ ID NO: 13, polypeptides and fragments of p18 as shown in SEQ ID NOs: 14 and 15, respectively and polypeptides derived from p23 as shown in SEQ ID NO: 16.

Any of these target polypeptides when fused to a SlpA chaperone can be used in an immunoassay as a binding partner for the detection of an analyte like, e.g., antibodies against the target polypeptide or may be used as a standard or calibration material for immunoassays as described in further detail below.

A further embodiment of the invention is a method of producing a fusion protein said method comprising the steps of a) culturing host cells comprising at least one nucleotide sequence coding for a target polypeptide and upstream thereto at least one nucleotide sequence coding for a SlpA chaperone, b) expression of said fusion protein, c) purification of said fusion protein and d) refolding into a soluble and native-like or immunoreactive (i.e., antigenic) conformation. A fusion protein produced by this method is also an aspect of the invention.

The fusion proteins according to the invention exhibit high solubility. When over expressed at a low rate in the cytosol they mainly accumulate in the soluble fraction. Depending on the conditions of cell growth and induction, especially when heavily over expressed, the SlpA-X gene products may also accumulate in inclusion bodies. Customarily, the skilled artisan aims at the overproduction of soluble target polypeptides in the *E. coli* cytosol. Cells are then disrupted by sonication or a combined lysozyme/EDTA treatment and the putatively native-like folded target proteins are isolated from the soluble fraction. This is feasible for SlpA-X fusion proteins and leads to soluble material in case the target polypeptide X possesses a sufficiently high intrinsic solubility. In case the target polypeptide X is very hydrophobic and strongly tends to aggregate, an alternative strategy may be applied which exploits the efficient and robust refolding properties of SlpA in a matrix-assisted renaturation approach. Cells are lysed under appropriate buffer conditions like, e.g., in chaotropic substances, which are strongly denaturing and solubilize even hydrophobic cell components and also the inclusion bodies, albeit at the expense of structural integrity. When the fusion proteins are N- or C-terminally tagged with a hexa-histidine (SEQ ID NO: 18) moiety, they may be specifically bound in an unfolded state to a metal-containing column (Ni-NTA or $Zn^{2+}$ or $Cu^{2+}$ supports). Immobilized to the solid phase, the molecules are easily and efficiently refolded under appropriate buffer conditions. This so-called matrix-assisted renaturation, which has been shown to increase the refolding yield of many difficult proteins, is strongly supported by the covalently linked SlpA, which, by virtue of its chaperone properties, possibly recognizes and reversibly masks hydrophobic patches in folding intermediates. Appropriate purification and refolding protocols as shown in more detail in the Examples section are well known to the skilled artisan.

A further aspect of the invention relates to any complex comprising SlpA and target polypeptide sequence, which includes addition of SlpA to any protein formulation. A further aspect of the invention relates to a recombinantly produced fusion protein comprising at least one polypeptide sequence corresponding to SlpA and at least one polypeptide sequence corresponding to a target polypeptide. A further aspect of the invention relates to a synthetically produced SlpA either alone or in combination with a target polypeptide of recombinant or synthetic origin.

According to the invention, a SlpA chaperone is able to improve the thermal stability of difficult target polypeptides when used as a fusion partner. SlpA confers thermal stability on a fused target polypeptide thereby making the target polypeptide less susceptible to heat-induced aggregation as shown in the Examples section. When strongly aggregation-prone target proteins fused to E. coli SlyD are subjected to thermal stress, the resulting fusion proteins show an onset of thermally-induced aggregation at about 42° C., which is in fair agreement with the inherent stability of SlyD. When the same target proteins are fused to SlpA, preferably to E. coli SlpA, they remain stable and soluble up to around 56° C. For example, a fusion protein containing SlyD and the fragment 536-681 from the HIV protein gp41 (SEQ ID NO: 5) starts to aggregate at a temperature of 42° C. whereas the same target protein fused to E. coli SlpA (SEQ ID NO: 3) according to the invention is thermally stable at temperatures beyond 50° C. It can be shown that SlpA as part of a fusion protein protects difficult or aggregation-prone proteins against aggregation following heat-induced denaturation.

Figure 7:
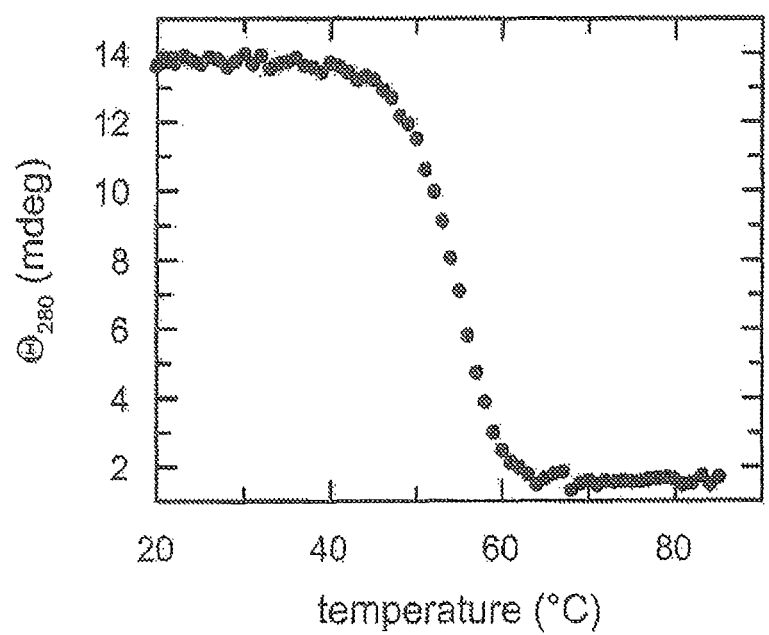
FIG. 7: Thermally induced unfolding transition of SlyD-gG1 (26-189) as monitored by near-UV CD at 280 nm. The ellipticity of the fusion protein as a function of temperature is given in millidegrees (mdeg). Unfolding of SlyD-gG1 (26-189) is largely reversible, and the near-UV CD signal of the native fusion polypeptide is restored to a large extent when the sample is chilled to ambient temperature. The melting temperature (i.e., the temperature at which 50% of the molecules are folded and 50% are unfolded) of SlyD-gG1 (26-189) approximates to 53° C.
Figure 8:
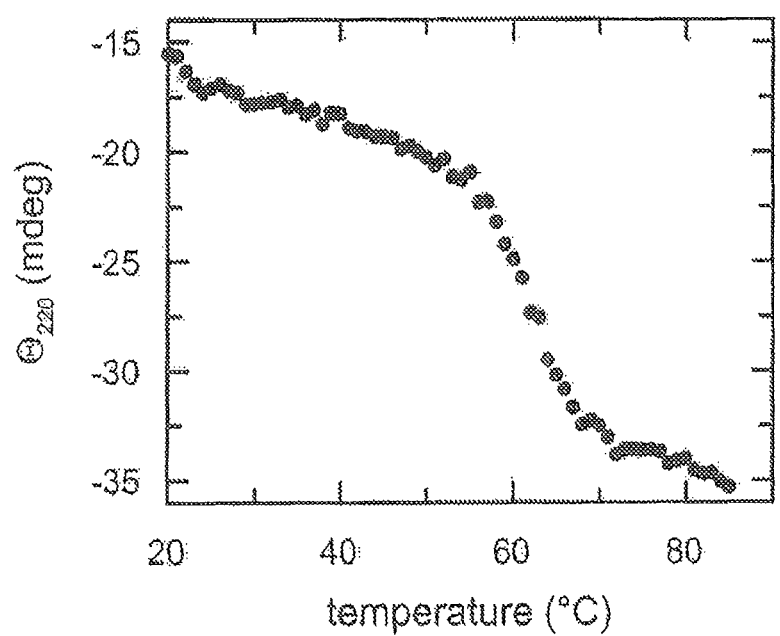
FIG. 8: Thermally induced unfolding transition of SlpA-gG1 (26-189) as monitored by far-UV CD at 220 nm. The ellipticity of the fusion protein as a function of temperature is given in millidegrees (mdeg). Unfolding of SlpA-gG1 (26-189) is largely reversible, and the far-UV CD signal of the native fusion polypeptide is restored to a large extent when the sample is cooled to room temperature. The melting temperature (i.e., the temperature at which 50% of the molecules are folded and 50% are unfolded) of SlpA-gG1 (26-189) approximates to 63° C. This clearly illustrates the superior thermal stability of SlpA-gG1 (26-189) when compared to SlyD-gG1 (26-189).

It can also be shown that fusion of SlpA exerts a beneficial effect even on proteins or protein fragments that are less aggregation-prone. When the glycoprotein G1 fragment gG1 (26-189) from HSV-1 is fused to SlyD, the resulting fusion protein can be thermally unfolded in a largely reversible fashion with an approximate melting temperature at 53° C. (FIG. 7). When, however, the same fragment is fused to SlpA, the resulting fusion protein shows a midpoint of thermally induced unfolding at approximately 63° C. (FIG. 8). Obviously, the stability of the gG1 fusion polypeptide is shifted by 10° C. upon substitution of SlpA for SlyD as a fusion partner. This finding clearly demonstrates the superior stability features of a SlpA-X fusion polypeptide compared to its SlyD-X counterpart.

In order to elucidate whether these superior stability features of SlpA fusion polypeptides are also reflected in an immunoassay, thermally challenged samples of SlyD-gG1 and SlpA-gG1 were assessed with anti-HSV positive and negative human sera (Example 4) for their immunoreactivity recovered after heat-stress. When compared with unstressed samples, a clear result was observed (see Example 4 and FIG. 9): The signal generated by heat-treated SlyD-gG1 and SlpA-gG1 with anti-HSV positive sera was reduced in all cases, but the signal loss was much more pronounced with the SlyD fusion variant. In turn, the background signal generated by heat-treated SlyD-gG1 and SlpA-gG1 with anti-HSV negative sera was increased in all cases (indicative of aggregation processes of the ruthenium-conjugated antigen), but the increase in signal height was again much more pronounced with the SlyD fusion variant. With respect to the signal readout for both the positive and the negative sera (i.e., with respect to the signal dynamics), SlpA is therefore clearly superior to SlyD as a fusion partner for gG1 (26-189). Obviously, the use of SlpA instead of SlyD as a fusion partner ensures both a lower signal level with negative sera and a higher signal recovery with positive sera. Briefly, the use of SlpA as a fusion partner warrants excellent signal dynamics even after harsh treatment of an immunoassay kit containing polypeptide antigens for the detection of immunoglobulin analytes. It is well conceivable that SlpA or related chaperone modules that are covalently attached to their target molecules via sufficiently long and flexible cross-linkers (by means of standard chemical methods) exert a similar solubilizing effect. In such cases, where a fusion polypeptide is not feasible, the chaperone and the target molecule would be produced and refolded separately before being linked covalently.

A further aspect of the invention concerns the use of a recombinantly or synthetically produced fusion protein comprising an SlpA chaperone and a target polypeptide as a binding partner in an immunoassay. Immunoassays and various homogenous and heterogeneous test formats are well known to the skilled artisan. They can be carried out in all biological liquids known to someone skilled in the art. Preferred samples are body liquids like whole blood, blood sera, blood plasma, urine or saliva.

The fusion polypeptides comprising SlpA and at least one target polypeptide according to the invention may also be used as standard or calibration material. SlpA is also a good fusion partner for difficult proteins that are needed as calibrators in immunoassays. For instance, we cloned, expressed and purified a Troponin I variant (comprising residues 1-209) in fusion with SlpA. The resulting fusion polypeptide SlpA-Troponin I turned out to be soluble and immunoreactive and was well-suited as a standard calibrator material for an Troponin I immunoassay. Due to the SlpA fusion partner, the stability of the Troponin I moiety was substantially increased when compared to the isolated Troponin I, which is only marginally stable and spontaneously aggregates even under favorable buffer conditions. The use of SlpA in complex with difficult proteins to generate soluble and stable calibrator or standard materials is a further embodiment of the invention. Yet a further aspect is the use of SlpA as an additive to improve the solubility and prevent the aggregation of a target protein.

A further embodiment of the invention is a method for the detection of antibodies specific for an analyte in an isolated sample, said method comprising a) forming an immunoreaction admixture by admixing a body fluid sample with a fusion protein comprising at least one polypeptide sequence corresponding to a SlpA chaperone and at least one polypeptide sequence corresponding to a target polypeptide,
b) maintaining said immunoreaction admixture for a time period sufficient for allowing antibodies against said analyte present in the body fluid sample to immunoreact with said fusion protein to form an immunoreaction product; and
c) detecting the presence of any of said immunoreaction product.

In a preferred embodiment the detection of specific antibodies can be performed by the so-called double antigen sandwich test (DAGS; also called bridge test), a heterogeneous format wherein the specific antibody analyte to be determined forms a bridge between two identical or similar antigens. This format can readily be adapted for high-throughput automated analyzers. More specifically, the antibodies to be determined form an immunocomplex or immunoreaction product with a first antigen which mediates immobilization to a solid phase and with a second antigen carrying a label (i.e., a signaling moiety like a chromogenic, fluorescent, chemiluminescent, electrochemiluminescent or other labels that are known to someone skilled in the art) thus allowing quantitative or qualitative detection of the specifically bound antibodies after separation of the liquid and the solid phase. Therefore, only if the antibodies under investigation are present in the sample a bridge is formed, and a signal can be detected. In such an assay format the fusion proteins according to the invention can be used as binding partners wherein the solid phase-bound antigen or the labeled antigen or both are fusion proteins comprising an *E. coli* SlpA chaperone and a target polypeptide. The target polypeptide constitutes the antigenic part of the fusion protein.

A preferred embodiment of the invention is a so-called asymmetric double antigen sandwich test for the detection of a specific antibody wherein a first fusion protein and a second fusion protein each comprising a chaperone and a target polypeptide are used. This format is termed asymmetric because the chaperone units of both fusion proteins differ from each other. For instance, the first fusion protein may comprise at least one SlpA chaperone unit and at least one target polypeptide unit and may bear a moiety that mediates specific binding to a solid phase like, e.g., biotin that binds to a streptavidin-coated solid phase. The second fusion protein may comprise at least one chaperone unit different from SlpA and at least one target polypeptide unit that is identical or similar to the target polypeptide of the first fusion protein. In addition, the latter fusion protein may carry a signaling moiety or a reporter group for signal readout.

Preferably, the chaperone unit of the second fusion protein is also a thermostable chaperone with sufficient intrinsic flexibility (i.e., highly dynamic binding activity) at ambient temperature. Suitable candidates for the chaperone unit of the second fusion protein are for example FkpA (melting temperature around 50° C.) and a C-terminally truncated (cysteine-free) variant of the SlyD orthologue from *Pasteurella multocida* (melting temperature around 49° C.). The amino acid sequences of both chaperones (complete sequences and partial sequences preferably used as chaperone unit in a fusion protein) are shown in SEQ ID NOs. 9 to 12. The chaperone unit of the first and second fusion protein, may be exchanged, i.e., SlpA may be part of the second fusion protein and in this case the other thermostable chaperone like, e.g., FkpA or the SlyD orthologue of *Pasteurella multocida* may be part of the first fusion protein. The first and second fusion proteins are added, simultaneously or consecutively, to a sample under investigation for a specific antibody analyte. The antibody when present in the sample binds to the target polypeptide units of the first and the second fusion protein thereby bridging the target polypeptide parts of said first and said second fusion proteins resulting in an immunoreaction product or immunocomplex.

Before, after or concomitant with the formation of an immunocomplex, a solid phase like, e.g., microbeads or an ELISA plate is added so that the first fusion protein binds to the solid phase. As a consequence the whole immunoreaction product (i.e., the immunocomplex) comprising said first fusion protein, the antibody to be detected and said second fusion protein binds to the solid phase. After separation of the solid phase from the liquid phase the presence of the immunoreaction product can be detected. As an alternative, the chaperone units present in the first fusion protein may be used as chaperone units for the second fusion protein and vice versa. However, the chaperone units should preferably be different in both fusion proteins because of possible (unpredictable) non-analyte specific cross-linking of the fusion proteins due to the presence of antibodies against these chaperones in the sample. As an alternative, a highly specific DAGS immunoassay would also be feasible with identical chaperone fusion partners on either side of the assay. In this scenario, the developer of the assay must take into account as highly probable that antibodies against the used fusion partner are present in a substantial fraction of human sera. These antibodies would bridge the signaling polypeptide to the solid phase, raise the signal and thus evoke falsely positive results. In order to avoid such interferences, the fusion partner (i.e., the chaperone unit) would be added to the sample in a highly polymerized and unlabeled form as an anti-interference substance. The anti-interference substance is designed to efficiently capture immunoglobulins directed against the fusion partner, the linker segments, the spacer and tag sequences and all other moieties which are not part of the genuine antigen. By virtue of its high epitope density, a chemically polymerized (i.e., cross-linked) anti-interference substance is able to efficiently compete with the labeled fusion polypeptide for the binding of anti-chaperone antibodies. This way, interferences due to immunoglobulins with unwanted specificities can be ruled out in a convenient and reliable fashion. As a sample all biological liquids like body fluids may be used. Preferably, blood, serum, plasma, urine or saliva are used.

The labeling or signaling group can be selected from any known detectable marker groups, such as dyes, luminescent labeling groups such as chemiluminescent groups, e.g., acridinium esters or dioxetanes, or fluorescent dyes, e.g., fluorescein, coumarin, rhodamine, oxazine, resorufin, cyanine and derivatives thereof. Other examples of labeling groups are luminescent metal complexes, such as ruthenium or europium complexes, enzymes, e.g., as used for ELISA or radioisotopes.

The attachment of the immunocomplex or immunoreaction product to the solid phase may be carried out using one partner of a bioaffinity binding pair like, e.g., biotin and streptavidin. Preferably, biotin is coupled to the fusion protein according to the invention. This biotin-fusion protein-conjugate binds with high affinity to a streptavidin coated solid phase.

Examples of analytes are all pathogens and antibodies against these pathogens mentioned under the "target polypeptide" section. For example, according to the invention preferably antibodies against HIV (human immunodeficiency virus), HTLV-1/HTLV-II (human T-cell lymphotropic virus I & II), HCV (hepatitis C virus), HBV (hepatitis B virus), HAV (hepatitis A virus), HCMV (human cytomegalic virus), HSV-1/-2 (herpes simplex virus 1 & 2), EBV (Epstein-Barr virus), varicella zoster virus, human herpesvirus 6, human herpesvirus 7, human herpesvirus 8, rubella virus, *Treponema pallidum*, *Helicobacter pylori*, *Borrelia* (*burgdorferi*, *afzelii*, *garinii*), *Trypanosoma cruzi*, and *Toxoplasma gondii* can specifically be detected.

Yet another embodiment of the invention is a reagent kit for the detection of antibodies against an analyte, containing a fusion protein comprising at least one polypeptide sequence corresponding to SlpA and at least one polypeptide sequence corresponding to a target peptide. Further parts of such a reagent kit are known to someone skilled in the art and include buffers, preservatives, labeling substances and instructions for use.

Further embodiments of the invention include the use of a recombinantly or synthetically produced fusion protein according to the invention as a means for the reduction of interferences in an immunoassay and its use for immunization of laboratory animals and the production of a vaccine.

Another embodiment of the invention relates to a composition comprising a recombinantly or synthetically produced fusion protein comprising at least one polypeptide sequence corresponding to SlpA and at least one polypeptide sequence corresponding to a target peptide and a pharmaceutically acceptable excipient.

According to the invention SlpA can be used as a folding helper for target polypeptides by adding SlpA in purified form to a target polypeptide, which includes addition of SlpA to any protein formulation as a stabilizing or solubilizing agent. For example, SlpA and related folding helpers from the FKBP family of peptidyl-prolyl-cis/trans isomerases can be added during or after the process of biotechnological production of target polypeptides thereby conferring solubility or thermal stability to the target polypeptide. Such biotechnological applications include for example large-scale industrial production of enzymes, peptide hormones such as, e.g., insulin, or, more generally, proteins of commercial interest.

In a further embodiment of the invention SlpA can be used as an additive in immunoassays to reduce or suppress immunological cross-reactions or interferences that evoke erroneously positive results, particularly in a double antigen sandwich immunoassay format.

More specifically, in an immunoassay SlpA-X or SlpA-SlpA-X fusion proteins may be used as antigens for the detection of an immunoglobulin analyte wherein X is the target polypeptide to which the analyte-specific antibodies bind. To reduce interferences, SlpA or SlpA-SlpA would be added as an anti-interference substance to avoid immunological cross-reactions via the chaperone unit. Preferably, SlpA or SlpA-SlpA would be added in a chemically polymerized form in order to increase the epitope density and to foster the binding of IgG and IgM molecules directed to SlpA, the linker segments or the hexa-histidine tag (SEQ ID NO: 18).

SlpA confers solubility and stability on target molecules, but it might, as any other moiety or group different from the very target molecule, evoke immunological cross-reactions that compromise the specificity of the respective immunoassay. In order to overcome this specificity problem, an unlabeled variant of SlpA or SlpA-SlpA is implemented in the immunoassay reagents in a polymerized form. This SlpA or SlpA-SlpA polypeptide comprises all of the elements that might evoke cross-reactions such as the SlpA unit itself, any linker or spacer segments, the hexa-histidine (SEQ ID NO: 18) or other tag motifs and even the label moieties, albeit in an inactivated form. Due to chemical cross-linking, these potential interference-prone motifs are presented to the cross-reacting antibodies in a high epitope density, which is well-suited to bind to and thus neutralize these potentially interfering antibodies. Besides this anti-interference effect, the SlpA or SlpA-SlpA polymer may even have additional advantageous effects: as a highly polymeric chaperone it should be able to adsorb to hydrophobic surface areas of any solid surface (such as beads, microtiter plates and tube or vessel walls) and thus reduce unspecific adsorption of the essential immunological components. Further, it may contribute to the solubility of other immunological components by virtue of its chaperone features, which might even be more pronounced in its polymerized form.

The examples that follow illustrate the invention further.

Example 1

Cloning and Purification of SlpA and SlyD Fusion Polypeptides

Cloning of Expression Cassettes

On the basis of the pET24a expression plasmid of Novagen (Madison, Wis., USA) an expression cassette encoding the SlyD or SlpA fusion polypeptides was obtained. The sequence of the gp41 ectodomain was retrieved from the SwissProt database. A synthetic gene encoding gp41 (aa 536-681) with a glycine-rich linker region fused in frame to the N-terminus was purchased from Medigenomix (Martinsried, Germany). BamHI and XhoI restriction sites were at the 5' and the 3' ends of the coding region, respectively. A further synthetic gene encoding two SlpA units (residues 1-146 and 2-149 according to SEQ ID NO: 1, SwissProt accession no. P0AEM0) connected via a glycine-rich linker region and encompassing part of a further linker region at the C-terminus were likewise purchased from Medigenomix. NdeI and BamHI restriction sites were at the 5' and 3' ends of this cassette, respectively. The genes and the restriction sites were designed to enable the in frame fusion of SlpA-SlpA and the gp41 ectodomain fragment by simple ligation. In order to avoid inadvertent recombination processes and to increase the genetic stability of the expression cassette in the *E. coli* host, the nucleotide sequences encoding the SlpA units were degenerated as well as the nucleotide sequences encoding the extended linker regions. i.e., different codon combinations were used to encode identical amino acid sequences.

The pET24a vector was digested with NdeI and XhoI and the cassette comprising tandem-SlpA fused in frame to the HIV-1 gp41 ectodomain fragment 536-681 was inserted. Expression cassettes comprising SlyD or tandem SlyD instead of SlpA or tandem SlpA were constructed accordingly, as well as expression cassettes comprising target polypeptides different from gp41. All recombinant fusion polypeptide variants contained a C-terminal hexahistidine tag (SEQ ID NO: 18) to facilitate Ni-NTA-assisted purification and refolding. QuikChange (Stratagene, La Jolla, Calif., USA) and standard PCR techniques were used to generate point mutations, deletion and extension variants or restriction sites in the respective expression cassettes.

The drawing below shows a scheme of the resulting HIV-1 gp41 ectodomain fragment 536-681 bearing two tandem SlpA chaperones fused in frame to its N-terminal end.

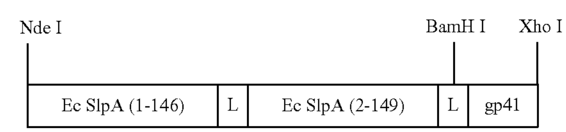

L = (GGGS)$_5$GGG-Linker

The insert of the resulting plasmid was sequenced and found to encode the desired fusion protein. The complete amino acid sequence is shown in SEQ ID NO: 4. The amino acid sequence of the linker L is shown is SEQ ID NO: 17.

Purification of SlpA, SlyD and Fusion Proteins Comprising SlpA, SlyD, and FkpA SlyD, SlpA, and all fusion protein variants were purified by using virtually identical protocols. *E. coli BL*21 (DE3) cells harboring the particular pET24a expression plasmid were grown at 37° C. in LB medium plus kanamycin (30 μg/ml) to an $OD_{600}$ of 1.5, and cytosolic over expression was induced by adding 1 mM isopropyl-β-D-thiogalactoside. Three hours after induction, cells were harvested by centrifugation (20 mM at 5000 g), frozen and stored at −20° C. For cell lysis, the frozen pellet was resuspended in chilled 50 mM potassium phosphate pH 8.0, 7.0 M GdmCl, 5 mM imidazole and the suspension was stirred for 2 h on ice to complete cell lysis. After centrifugation and filtration (cellulose nitrate membrane, 0.45 μm/0.2 μm), the lysate was applied onto a Ni-NTA column equilibrated with the lysis buffer including 5.0 mM TCEP. The subsequent washing step was tailored for the respective target protein and ranged from 5-15 mM imidazole in 50 mM potassium phosphate pH 8.0, 7.0 M GdmCl, 5.0 mM TCEP. At least 10-15 volumes of the washing buffer were applied. Then, the GdmCl solution was replaced by 50 mM potassium phosphate pH 7.8, 100 mM KCl, 10 mM imidazole, 5.0 mM TCEP to induce conformational refolding of the matrix-bound protein. In order to avoid reactivation of copurifying proteases, a protease inhibitor cocktail (Complete EDTA-free, Roche) was included in the refolding buffer. A total of 15-20 column volumes of refolding buffer were applied in an overnight reaction. Then, both TCEP and the Complete EDTA-free inhibitor cocktail were removed by washing with 3-5 column volumes 50 mM potassium phosphate pH 7.8, 100 mM KCl, 10 mM imidazole. The native protein was then eluted by 250 mM imidazole in the same buffer. Protein-containing fractions were assessed for purity by Tricine-SDS-PAGE and pooled. Finally, the proteins were subjected to size-exclusion-chromatography (SUPERDEX HiLoad, GE Healthcare Bio-Sciences AB) and the protein-containing fractions were pooled and concentrated in an Amicon cell (YM10).

After the coupled purification and refolding protocol, yields of roughly 5-20 mg could be obtained from 1 g of *E. coli* wet cells, depending on the respective target protein.

Example 2

Spectroscopic Measurements

Circular dichroism spectroscopy (CD) is the method of choice to assess both the secondary and the tertiary structure in proteins. Ellipticity in the aromatic region (260-320 nm) reports on tertiary contacts within a protein (i.e., the globular structure of a regularly folded protein), whereas ellipticity in the amide region (190-250 nm) reflects regular repetitive elements in the protein backbone, i.e., the secondary structure.

Protein concentration measurements were performed with an Uvikon XL double-beam spectrophotometer. The molar extinction coefficients ($\epsilon_{280}$) were determined by using the procedure described by Pace (1995), Protein Sci. 4, 2411-2423.

Near-UV CD spectra were recorded with a Jasco-720 spectropolarimeter with a thermostated cell holder and converted to mean residue ellipticity. The buffer was 50-150 mM potassium phosphate pH 7.5, 100 mM KCl, 1 mM EDTA. The path length was 0.5 cm or 1.0 cm, the protein concentration was 20-500 µM. The band width was 2 nm, the scanning speed was 50 nm/min at a resolution of 0.5 nm and the response was 1 or 2 s. In order to improve the signal-to-noise ratio, spectra were measured nine times and averaged.

Far-UV CD spectra were recorded with a Jasco-720 spectropolarimeter with a thermostated cell holder and converted to mean residue ellipticity. The buffer was 10 mM potassium phosphate pH 7.5, 25 mM KCl, 0.5 mM EDTA. The path length was 0.2 cm, the protein concentration ranged between 2.5 and 20 µM. The band width was 2 nm, the scanning speed was 50 nm/min at a resolution of 0.5 nm and the response was 1 or 2 s. In order to improve the signal-to-noise ratio, spectra were measured nine times and averaged.

Example 3

Coupling of Biotin and Ruthenium Moieties to the Fusion Proteins

The lysine ε-amino groups of the fusion polypeptides were modified at protein concentrations of 10-20 mg/ml with N-hydroxy-succinimide activated biotin and ruthenium labels, respectively. The label/protein ratio varied from 2:1 to 5:1 (mol:mol), depending on the respective fusion protein. The reaction buffer was 150 mM potassium phosphate pH 8.0, 100 mM KCl, 1 mM EDTA. The reaction was carried out at room temperature for 15 mM and stopped by adding buffered L-lysine to a final concentration of 10 mM. To avoid hydrolytic inactivation of the labels, the respective stock solutions were prepared in dried DMSO (seccosolv quality, Merck, Germany). DMSO concentrations up to 15% in the reaction buffer were well tolerated by all fusion proteins studied. After the coupling reaction, unreacted free label was removed by passing the crude protein conjugate over a gel filtration column (SUPERDEX 200 HiLoad).

Example 4

Immunological Reactivity of the Polypeptide Fusion Proteins

The immunological reactivity (i.e., the antigenicity) of the different fusion proteins was assessed in an automated ELECSYS 2010 analyzer (Roche Diagnostics GmbH). Measurements were carried out in the double antigen sandwich format.

Signal detection in ELECSYS 2010 is based on electrochemiluminescence. The biotin-conjugate (i.e., the capture-antigen) is immobilized on the surface of a streptavidin coated magnetic bead whereas the detection-antigen bears a complexed Ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in arbitrary light units.

Fusion polypeptides containing HSV-1 antigen gG1 (amino acids 26-189, see SEQ ID NOs: 7 and 8) as HSV-1 specific antigenic sequence were used in the assay for both the capture and the detection antigen. The gG1 antigen was either fused to SlpA or SlyD. In the double antigen sandwich immunoassay, a SlpA-gG1 (26-189)-biotin conjugate was applied together with a SlpA-gG1 (26-189)-ruthenium complex conjugate (invention) at a concentration of 100 ng/ml each. As well, a SlyD-gG1 (26-189)-biotin conjugate was applied together with a SlyD-gG1 (26-189)-ruthenium complex conjugate (comparison) at a concentration of 100 ng/ml each.

The biotin and the ruthenium conjugates of the fusion polypeptide variants of gG1 (26-189) were assessed for their reactivity against anti-HSV-1 positive sera at concentrations of 100 ng/ml each. In all measurements, unlabeled chemically polymerized SlyD-SlyD was implemented in the reaction buffer as an anti-interference substance to avoid immunological cross reactions via the chaperone fusion unit. Eleven anti-HSV-1 negative human sera were used as controls.

To ascertain the thermo tolerance of the fusion proteins, SlyD-gG1 and SlpA-gG1 were subjected to harsh temperature conditions as follows: SlyD-gG1 and SlpA-gG1 (proteins in 50 mM potassium phosphate pH 7.5, 100 mM KCl, 1 mM EDTA) were incubated overnight at 60° C. The concentration of the gG1-biotin conjugates was roughly 1.3 mg/ml each, the concentration of the gG1-ruthenium conjugates was roughly 0.6 mg/ml each. Subsequently, the thermally stressed samples were assessed for their residual immunological reactivity in an ELECSYS 2010 automated analyzer under the experimental conditions described above. Unchallenged samples (stored at 2-8° C.) of SlyD-gG1 and SlpA-gG1 were used as a reference.

The outcome of the experiments is shown in Table 1 (FIG. 9).

Table 1 depicts the immunological reactivity of SlpA-gG1 (26-189) and SlyD-gG1 (26-189) with human anti-HSV-1 positive and anti-HSV-1 negative sera in an automated ELEC-SYS analyzer as described in Example 4. Shown is the performance of both antigen variants before and after a harsh overnight heat-treatment at 60° C. The outcome of the experiments clearly demonstrates the superiority of heat-stressed SlpA-gG1 (26-189) over heat-stressed SlyD-gG1 (26-189) in a twofold manner. Firstly, the specific signal recovery with anti-HSV-1 positive sera (upper half of Table 1) is significantly higher with the heat-challenged SlpA fusion polypeptide. Secondly, the increase in unspecific background signal with anti-HSV-1 negative sera (lower half of Table 1) is significantly lower with the heat-challenged SlpA fusion polypeptide. We observe a considerable increase in the background signal after heat-treatment of the SlyD fusion polypeptides (see right column, about 100 to 900% increase in the background signal).

When using SlpA fusion polypeptides according to the invention, however, the increase in background signal after heat stress is negligibly low, i.e., it is below 20% in all but one cases. In that one case, (serum sample Trina 07/06-533) there is an increase in background signal of 48%. The very same sample (Trina 07/06-533) shows an increase in background signal of more than 800% when the SlyD fusion polypeptide is used instead. This shows that even with difficult samples that inherently evoke slightly elevated background signals SlpA fusion polypeptides can substantially reduce the background signal. Low background signals are highly desired in the development of immunoassays because they enable the manufacturer to set a low cut-off value. Generally, reduced background signals are required for an increased assay performance with respect to sensitivity. The reason is that samples yielding a signal above the cut-off value are considered as positive (i.e., the samples are assumed to contain the analyte under study); samples yielding a signal below the cut-off value are considered as negative. It is therefore easy to understand why a low cut-off is utterly needed: the lower the cut-off is, the higher is the probability that samples that contain low analyte concentrations (and concomitantly yield low signals) will be correctly found as low positive. Thus, the sensitivity of an immunoassay may be increased by lowering the background signal that inherently originates from its immunological components. The use of SlpA as a folding helper thus clearly contributes to improve and warrant the long-term sensitivity of an immunoassay.

To sum up, fusion polypeptides containing SlpA increase both the stability and the solubility of the fused target polypeptides, in particular under critical conditions (such as thermal stress), which usually would compromise the native fold and lead to aggregation processes. In brief, SlpA is an excellent folding helper which protects the integrity of its client proteins even under very unfavorable conditions, facilitates their refolding into an active conformation and keeps them in solution. Fusion to SlpA or, more simply, addition of SlpA is therefore an excellent means to stabilize target molecules in protein formulations intended for diagnostic and other biotechnological purposes.

What is claimed is:

1. A method of detecting an analyte within a sample, comprising:
   contacting, in vitro, a sample with a first recombinant fusion protein comprising a chaperone polypeptide and a target polypeptide, the target polypeptide having specific binding affinity for an analyte within the sample;
   exposing a solid phase support to a mixture including the sample and the first recombinant fusion protein, the first recombinant fusion protein having binding affinity for a solid phase support;
   contacting, in vitro, the sample with a second recombinant fusion protein comprising a chaperone polypeptide, a target polypeptide, and a signaling moiety, the target polypeptide having specific binding affinity for the analyte within the sample and the chaperone polypeptide of the second recombinant fusion protein being different from the chaperone polypeptide of the first recombinant fusion protein, wherein one of the chaperone polypeptide of the first recombinant fusion protein and the chaperone polypeptide of the second recombinant fusion protein is a SlpA polypeptide; and
   detecting a signal from the signaling moiety of the second recombinant fusion protein bound to analyte bound to the first recombinant fusion protein bound to the solid phase support.

2. The method of claim 1 further comprising the step of contacting, in vitro, the sample with a polymerized, unlabeled chaperone protein prior to said steps of contacting with the first recombinant fusion protein and contacting with the second recombinant fusion protein, the polymerized, unlabeled chaperone protein comprising a substantially identical amino acid sequence as one of the chaperone protein of the first recombinant fusion protein and the chaperone protein of the second recombinant fusion protein.

3. The method of claim 1, wherein the chaperone polypeptide of the other of the first and second recombinant fusion protein is one of FkpA polypeptide and Pasteurella multocida SlyD polypeptide.

4. The method of claim 1, wherein the target polypeptide of the first and second recombinant fusion proteins comprise one of a herpes simplex virus 1 antigen gG 1, a herpes simplex virus 2 antigen gG2, and an Epstein-Ban virus nuclear antigen 1.

5. The method of claim 1, wherein said steps of contacting with the first recombinant fusion protein and contacting with the second recombinant fusion protein occur substantially simultaneously.

6. The method of claim 1, wherein the SlpA polypeptide comprises amino acid SEQ ID NO: 2.

7. The method of claim 1, wherein the SlpA polypeptide consists of amino acids 1-147 of SEQ ID NO: 2.

8. The method of claim 1, wherein the SlpA polypeptide N-terminally starts with an amino acid located between amino acids 59 and 78 of SEQ ID NO: 2 and C-terminally ending with an amino acid located between amino acids 125 and 139 of SEQ ID NO: 2.

9. The method of claim 1, wherein at least one of the first recombinant fusion protein and the second recombinant fusion protein further comprise a linker polypeptide, the linker polypeptide linking the chaperone polypeptide with the target polypeptide.

10. The method of claim 9, wherein the linker polypeptide comprises less than one hundred amino acids.

11. The method of claim 9, wherein the linker polypeptide comprises SEQ ID NO: 17.

12. The method of claim 1, wherein the solid phase support consists of one of microbeads and micro-wells.

13. The method of claim 1, wherein the first recombinant fusion protein further comprises a solid phase binding moiety having specific binding affinity for an exposed moiety of the solid phase support.

14. The method of claim 13, wherein the solid phase binding moiety consists of one of biotin and streptavidin and the solid phase support comprises an exposed moiety comprising one of an other of biotin and streptavidin.

15. The method of claim 1, wherein the signaling moiety comprises at least one of a dye and a luminescent label.

16. The method of claim 1, wherein the signaling moiety comprises a luminescent label selected from the group consisting of acridinium ester, dioxetane, ruthenium metal complex, europium metal complex, and a radioisotope.

17. The method of claim 1, wherein the sample is selected from the group consisting of blood, serum, plasma, urine, and saliva.

18. A method of detecting an analyte within a sample, comprising:
   contacting, in vitro, a sample with a first recombinant fusion protein and a second recombinant fusion protein each comprising a chaperone polypeptide and a target polypeptide, the target polypeptide of the first and second recombinant fusion proteins having specific binding affinity for an analyte within the sample, the chaperone polypeptide of the second recombinant fusion protein being different from the chaperone polypeptide of the first recombinant fusion protein, wherein one of the chaperone polypeptide of the first recombinant fusion protein and the second recombinant fusion protein is a SlpA polypeptide;

exposing a solid phase support to a mixture including the sample and the first and the second recombinant fusion proteins, the first recombinant fusion protein having binding affinity for a solid phase support, the second recombinant fusion protein comprising a signaling moiety; and detecting a signal from the signaling moiety of the second recombinant fusion protein bound to analyte bound to the first recombinant fusion protein bound to the solid phase support.

19. The method of claim 18, further comprising the step of contacting, in vitro, the sample with a polymerized, unlabeled chaperone protein prior to said steps of contacting with the first recombinant fusion protein and contacting with the second recombinant fusion protein, the polymerized, unlabeled chaperone protein comprising a substantially identical amino acid sequence as one of the chaperone protein of the first recombinant fusion protein and the chaperone protein of the second recombinant fusion protein.

20. The method of claim 18, wherein the target polypeptide of the first and second recombinant fusion proteins comprise one of a herpes simplex virus 1 antigen gG1, a herpes simplex virus 2 antigen gG2, and an Epstein-Barr virus nuclear antigen 1.

* * * * *

SEQUENCE LISTING

```
<160> NUMBER OF SEQ ID NOS: 18

<210> SEQ ID NO 1
<211> LENGTH: 149
<212> TYPE: PRT
<213> ORGANISM: Escherichia coli

<400> SEQUENCE: 1

Met Ser Glu Ser Val Gln Ser Asn Ser Ala Val Leu Val His Phe Thr
1               5                   10                  15

Leu Lys Leu Asp Asp Gly Thr Thr Ala Glu Ser Thr Arg Asn Asn Gly
            20                  25                  30

Lys Pro Ala Leu Phe Arg Leu Gly Asp Ala Ser Leu Ser Glu Gly Leu
        35                  40                  45

Glu Gln His Leu Leu Gly Leu Lys Val Gly Asp Lys Thr Thr Phe Ser
    50                  55                  60

Leu Glu Pro Asp Ala Ala Phe Gly Val Pro Ser Pro Asp Leu Ile Gln
65                  70                  75                  80

Tyr Phe Ser Arg Arg Glu Phe Met Asp Ala Gly Glu Pro Glu Ile Gly
                85                  90                  95

Ala Ile Met Leu Phe Thr Ala Met Asp Gly Ser Glu Met Pro Gly Val
            100                 105                 110

Ile Arg Glu Ile Asn Gly Asp Ser Ile Thr Val Asp Phe Asn His Pro
        115                 120                 125

Leu Ala Gly Gln Thr Val His Phe Asp Ile Glu Val Leu Glu Ile Asp
    130                 135                 140

Pro Ala Leu Glu Ala
145
```

```
<210> SEQ ID NO 2
<211> LENGTH: 153
<212> TYPE: PRT
<213> ORGANISM: Escherichia coli

<400> SEQUENCE: 2

Ser Glu Ser Val Gln Ser Asn Ser Ala Val Leu Val His Phe Thr Leu
1               5                   10                  15

Lys Leu Asp Asp Gly Thr Thr Ala Glu Ser Thr Arg Asn Asn Gly Lys
            20                  25                  30

Pro Ala Leu Phe Arg Leu Gly Asp Ala Ser Leu Ser Glu Gly Leu Glu
        35                  40                  45

Gln His Leu Leu Gly Leu Lys Val Gly Asp Lys Thr Thr Phe Ser Leu
    50                  55                  60

Glu Pro Asp Ala Ala Phe Gly Val Pro Ser Pro Asp Leu Ile Gln Tyr
65                  70                  75                  80

Phe Ser Arg Arg Glu Phe Met Asp Ala Gly Glu Pro Glu Ile Gly Ala
                85                  90                  95

Ile Met Leu Phe Thr Ala Met Asp Gly Ser Glu Met Pro Gly Val Ile
            100                 105                 110

Arg Glu Ile Asn Gly Asp Ser Ile Thr Val Asp Phe Asn His Pro Leu
        115                 120                 125

Ala Gly Gln Thr Val His Phe Asp Ile Glu Val Leu Glu Ile Asp Pro
    130                 135                 140

Ala Leu Glu His His His His His His
145                 150

<210> SEQ ID NO 3
<211> LENGTH: 323
<212> TYPE: PRT
<213> ORGANISM: Artificial Sequence
<220> FEATURE:
<223> OTHER INFORMATION: fusion protein of SlpA and HIV gp41

<400> SEQUENCE: 3

Met Ser Glu Ser Val Gln Ser Asn Ser Ala Val Leu Val His Phe Thr
1               5                   10                  15

Leu Lys Leu Asp Asp Gly Thr Thr Ala Glu Ser Thr Arg Asn Asn Gly
            20                  25                  30

Lys Pro Ala Leu Phe Arg Leu Gly Asp Ala Ser Leu Ser Glu Gly Leu
        35                  40                  45

Glu Gln His Leu Leu Gly Leu Lys Val Gly Asp Lys Thr Thr Phe Ser
    50                  55                  60

Leu Glu Pro Asp Ala Ala Phe Gly Val Pro Ser Pro Asp Leu Ile Gln
65                  70                  75                  80

Tyr Phe Ser Arg Arg Glu Phe Met Asp Ala Gly Glu Pro Glu Ile Gly
                85                  90                  95

Ala Ile Met Leu Phe Thr Ala Met Asp Gly Ser Glu Met Pro Gly Val
            100                 105                 110

Ile Arg Glu Ile Asn Gly Asp Ser Ile Thr Val Asp Phe Asn His Pro
        115                 120                 125

Leu Ala Gly Gln Thr Val His Phe Asp Ile Glu Val Leu Glu Ile Asp
    130                 135                 140

Pro Ala Gly Gly Gly Ser Gly Gly Gly Ser Gly Gly Ser Gly Gly
145                 150                 155                 160

Gly Ser Gly Gly Gly Ser Gly Gly Gly Thr Leu Thr Val Gln Ala Arg
                165                 170                 175
```

```
Gln Leu Leu Ser Gly Ile Val Gln Gln Asn Asn Glu Leu Arg Ala
                180                 185                 190

Ile Glu Ala Gln Gln His Leu Glu Gln Leu Thr Val Trp Gly Thr Lys
        195                 200                 205

Gln Leu Gln Ala Arg Glu Leu Ala Val Glu Arg Tyr Leu Lys Asp Gln
        210                 215                 220

Gln Leu Leu Gly Ile Trp Gly Cys Ser Gly Lys Leu Ile Cys Thr Thr
225                 230                 235                 240

Ala Val Pro Trp Asn Ala Ser Trp Ser Asn Lys Ser Leu Glu Gln Ile
                245                 250                 255

Trp Asn Asn Met Thr Trp Met Glu Trp Asp Arg Glu Ile Asn Asn Tyr
                260                 265                 270

Thr Ser Leu Ile His Ser Leu Ile Glu Glu Ser Gln Asn Gln Gln Glu
        275                 280                 285

Lys Asn Glu Gln Glu Leu Leu Glu Leu Asp Lys Trp Ala Ser Leu Trp
        290                 295                 300

Asn Trp Phe Asn Ile Thr Asn Trp Leu Trp Tyr Leu Glu His His His
305                 310                 315                 320

His His His

<210> SEQ ID NO 4
<211> LENGTH: 494
<212> TYPE: PRT
<213> ORGANISM: Artificial Sequence
<220> FEATURE:
<223> OTHER INFORMATION: fusion protein of SlpA SlpA and HIV gp41

<400> SEQUENCE: 4

Met Ser Glu Ser Val Gln Ser Asn Ser Ala Val Leu Val His Phe Thr
1               5                   10                  15

Leu Lys Leu Asp Asp Gly Thr Thr Ala Glu Ser Thr Arg Asn Asn Gly
                20                  25                  30

Lys Pro Ala Leu Phe Arg Leu Gly Asp Ala Ser Leu Ser Glu Gly Leu

```
Asp Ala Ser Leu Ser Glu Gly Leu Glu Gln His Leu Leu Gly Leu Lys
    210                 215                 220
Val Gly Asp Lys Thr Thr Phe Ser Leu Glu Pro Asp Ala Ala Phe Gly
225                 230                 235                 240
Val Pro Ser Pro Asp Leu Ile Gln Tyr Phe Ser Arg Arg Glu Phe Met
                245                 250                 255
Asp Ala Gly Glu Pro Glu Ile Gly Ala Ile Met Leu Phe Thr Ala Met
                260                 265                 270
Asp Gly Ser Glu Met Pro Gly Val Ile Arg Glu Ile Asn Gly Asp Ser
            275                 280                 285
Ile Thr Val Asp Phe Asn His Pro Leu Ala Gly Gln Thr Val His Phe
    290                 295                 300
Asp Ile Glu Val Leu Glu Ile Asp Pro Ala Leu Glu Ala Gly Gly Gly
305                 310                 315                 320
Ser Gly Gly Gly Ser Gly Gly Ser Gly Gly Ser Gly Gly
                325                 330                 335
Ser Gly Gly Gly Thr Leu Thr Val Gln Ala Arg Gln Leu Leu Ser Gly
            340                 345                 350
Ile Val Gln Gln Gln Asn Asn Glu Leu Arg Ala Ile Glu Ala Gln Gln
                355                 360                 365
His Leu Glu Gln Leu Thr Val Trp Gly Thr Lys Gln Leu Gln Ala Arg
    370                 375                 380
Glu Leu Ala Val Glu Arg Tyr Leu Lys Asp Gln Gln Leu Leu Gly Ile
385                 390                 395                 400
Trp Gly Cys Ser Gly Lys Leu Ile Cys Thr Thr Ala Val Pro Trp Asn
                405                 410                 415
Ala Ser Trp Ser Asn Lys Ser Leu Glu Gln Ile Trp Asn Asn Met Thr
                420                 425                 430
Trp Met Glu Trp Asp Arg Glu Ile Asn Asn Tyr Thr Ser Leu Ile His
        435                 440                 445
Ser Leu Ile Glu Glu Ser Gln Asn Gln Gln Glu Lys Asn Glu Gln Glu
    450                 455                 460
Leu Leu Glu Leu Asp Lys Trp Ala Ser Leu Trp Asn Trp Phe Asn Ile
465                 470                 475                 480
Thr Asn Trp Leu Trp Tyr Leu Glu His His His His His
                485                 490

<210> SEQ ID NO 5
<211> LENGTH: 342
<212> TYPE: PRT
<213> ORGANISM: Artificial Sequence
<220> FEATURE:
<223> OTHER INFORMATION: fusion protein of SlyD and gp41

<400> SEQUENCE: 5

Met Lys Val Ala Lys Asp Leu Val Val Ser Leu Ala Tyr Gln Val Arg
1               5                   10                  15
Thr Glu Asp Gly Val Leu Val Asp Glu Ser Pro Val Ser Ala Pro Leu
                20                  25                  30
Asp Tyr Leu His Gly His Gly Ser Leu Ile Ser Gly Leu Glu Thr Ala
            35                  40                  45
Leu Glu Gly His Glu Val Gly Asp Lys Phe Asp Val Ala Val Gly Ala
    50                  55                  60
Asn Asp Ala Tyr Gly Gln Tyr Asp Glu Asn Leu Val Gln Arg Val Pro
65                  70                  75                  80
```

```
Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
            115                 120                 125

Asn Leu Lys Phe Asn Val Glu Val Ala Ile Arg Glu Ala Thr Glu
        130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Thr Leu Thr Val
            180                 185                 190

Gln Ala Arg Gln Leu Leu Ser Gly Ile Val Gln Gln Gln Asn Asn Glu
        195                 200                 205

Leu Arg Ala Ile Glu Ala Gln Gln His Leu Glu Gln Leu Thr Val Trp
    210                 215                 220

Gly Thr Lys Gln Leu Gln Ala Arg Glu Leu Ala Val Glu Arg Tyr Leu
225                 230                 235                 240

Lys Asp Gln Gln Leu Leu Gly Ile Trp Gly Cys Ser Gly Lys Leu Ile
                245                 250                 255

Cys Thr Thr Ala Val Pro Trp Asn Ala Ser Trp Ser Asn Lys Ser Leu
            260                 265                 270

Glu Gln Ile Trp Asn Asn Met Thr Trp Met Glu Trp Asp Arg Glu Ile
        275                 280                 285

Asn Asn Tyr Thr Ser Leu Ile His Ser Leu Ile Glu Glu Ser Gln Asn
    290                 295                 300

Gln Gln Glu Lys Asn Glu Gln Glu Leu Leu Glu Leu Asp Lys Trp Ala
305                 310                 315                 320

Ser Leu Trp Asn Trp Phe Asn Ile Thr Asn Trp Leu Trp Tyr Leu Glu
                325                 330                 335

His His His His His His
            340

<210> SEQ ID NO 6
<211> LENGTH: 535
<212> TYPE: PRT
<213> ORGANISM: Artificial Sequence
<220> FEATURE:
<223> OTHER INFORMATION: fusion protein of SlyD SlyD and gp41

<400> SEQUENCE: 6

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95
```

```
Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
        130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
            165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
            210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
            245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
            290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Leu Ala His
            325                 330                 335

Gly His Val His Gly Ala His Asp His His Asp His Asp His Asp
            340                 345                 350

Gly Gly Gly Ser Gly Gly Gly Ser Gly Gly Gly Ser Gly Gly Gly Ser
            355                 360                 365

Gly Gly Gly Ser Gly Gly Gly Thr Leu Thr Val Gln Ala Arg Gln Leu
            370                 375                 380

Leu Ser Gly Ile Val Gln Gln Gln Asn Asn Leu Arg Ala Ile Glu
385                 390                 395                 400

Ala Gln Gln His Leu Glu Gln Leu Thr Val Trp Gly Thr Lys Gln Leu
            405                 410                 415

Gln Ala Arg Glu Leu Ala Val Glu Arg Tyr Leu Lys Asp Gln Gln Leu
            420                 425                 430

Leu Gly Ile Trp Gly Cys Ser Gly Lys Leu Ile Cys Thr Thr Ala Val
            435                 440                 445

Pro Trp Asn Ala Ser Trp Ser Asn Lys Ser Leu Glu Gln Ile Trp Asn
            450                 455                 460

Asn Met Thr Trp Met Glu Trp Asp Arg Glu Ile Asn Asn Tyr Thr Ser
465                 470                 475                 480

Leu Ile His Ser Leu Ile Glu Glu Ser Gln Asn Gln Gln Glu Lys Asn
            485                 490                 495

Glu Gln Glu Leu Leu Glu Leu Asp Lys Trp Ala Ser Leu Trp Asn Trp
            500                 505                 510
```

-continued

```
Phe Asn Ile Thr Asn Trp Leu Trp Tyr His Gly His Asp His Asp His
        515                 520                 525

Asp His His His His His His
    530                 535

<210> SEQ ID NO 7
<211> LENGTH: 343
<212> TYPE: PRT
<213> ORGANISM: Artificial Sequence
<220> FEATURE:
<223> OTHER INFORMATION: fusion protein of SlpA and HSV-1 antigen gG1

<400> SEQUENCE: 7

Met Ser Glu Ser Val Gln Ser Asn Ser Ala Val Leu Val His Phe Thr
1               5                   10                  15

Leu Lys Leu Asp Asp Gly Thr Thr Ala Glu Ser Thr Arg Asn Asn Gly
            20                  25                  30

Lys Pro Ala Leu Phe Arg Leu Gly Asp Ala Ser Leu Ser Glu Gly Leu
        35                  40                  45

Glu Gln His Leu Leu Gly Leu Lys Val Gly Asp Lys Thr Thr Phe Ser
    50                  55                  60

Leu Glu Pro Asp Ala Ala Phe Gly Val Pro Ser Pro Asp Leu Ile Gln
65                  70                  75                  80

Tyr Phe Ser Arg Arg Glu Phe Met Asp Ala Gly Glu Pro Glu Ile Gly
                85                  90                  95

Ala Ile Met Leu Phe Thr Ala Met Asp Gly Ser Glu Met Pro Gly Val
            100                 105                 110

Ile Arg Glu Ile Asn Gly Asp Ser Ile Thr Val Asp Phe Asn His Pro
        115                 120                 125

Leu Ala Gly Gln Thr Val His Phe Asp Ile Glu Val Leu Glu Ile Asp
    130                 135                 140

Pro Ala Leu Glu Gly Gly Gly Ser Gly Gly Gly Ser Gly Gly Gly Ser
145                 150                 155                 160

Gly Gly Gly Ser Gly Gly Gly Ser Gly Gly Gly Pro Thr Asn Val Ser
                165                 170                 175

Ser Thr Thr Gln Pro Gln Leu Gln Thr Thr Gly Arg Pro Ser His Glu
            180                 185                 190

Ala Pro Asn Met Thr Gln Thr Gly Thr Thr Asp Ser Pro Thr Ala Ile
        195                 200                 205

Ser Leu Thr Thr Pro Asp His Thr Pro Pro Met Pro Ser Ile Gly Leu
    210                 215                 220

Glu Glu Glu Glu Glu Glu Glu Gly Ala Gly Asp Gly Glu His Leu Glu
225                 230                 235                 240

Gly Gly Asp Gly Thr Arg Asp Thr Leu Pro Gln Ser Pro Gly Pro Ala
                245                 250                 255

Phe Pro Leu Ala Glu Asp Val Glu Lys Asp Lys Pro Asn Arg Pro Val
            260                 265                 270

Val Pro Ser Pro Asp Pro Asn Asn Ser Pro Ala Arg Pro Glu Thr Ser
        275                 280                 285

Arg Pro Lys Thr Pro Pro Thr Ile Ile Gly Pro Leu Ala Thr Arg Pro
    290                 295                 300

Thr Thr Arg Leu Thr Ser Lys Gly Arg Pro Leu Val Pro Thr Pro Gln
305                 310                 315                 320
```

```
His Thr Pro Leu Phe Ser Phe Leu Thr Ala Ser Pro Ala Leu Asp Leu
                325                 330                 335

Glu His His His His His His
            340

<210> SEQ ID NO 8
<211> LENGTH: 360
<212> TYPE: PRT
<213> ORGANISM: Artificial Sequence
<220> FEATURE:
<223> OTHER INFORMATION: fusion protein of SlyD and HSV-1 antigen gG1

<400> SEQUENCE: 8

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
        50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
            115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Pro Thr Asn Val
            180                 185                 190

Ser Ser Thr Thr Gln Pro Gln Leu Gln Thr Thr Gly Arg Pro Ser His
            195                 200                 205

Glu Ala Pro Asn Met Thr Gln Thr Gly Thr Thr Asp Ser Pro Thr Ala
            210                 215                 220

Ile Ser Leu Thr Thr Pro Asp His Thr Pro Pro Met Pro Ser Ile Gly
225                 230                 235                 240

Leu Glu Glu Glu Glu Glu Glu Gly Ala Gly Asp Gly Glu His Leu
                245                 250                 255

Glu Gly Gly Asp Gly Thr Arg Asp Thr Leu Pro Gln Ser Pro Gly Pro
            260                 265                 270

Ala Phe Pro Leu Ala Glu Asp Val Glu Lys Asp Lys Pro Asn Arg Pro
            275                 280                 285

Val Val Pro Ser Pro Asp Pro Asn Asn Ser Pro Ala Arg Pro Glu Thr
            290                 295                 300

Ser Arg Pro Lys Thr Pro Pro Thr Ile Ile Gly Pro Leu Ala Thr Arg
305                 310                 315                 320

Pro Thr Thr Arg Leu Thr Ser Lys Gly Arg Pro Leu Val Pro Thr Pro
                325                 330                 335
```

```
Gln His Thr Pro Leu Phe Ser Phe Leu Thr Ala Ser Pro Ala Leu Asp
            340                 345                 350

Leu Glu His His His His His His
        355                 360

<210> SEQ ID NO 9
<211> LENGTH: 199
<212> TYPE: PRT
<213> ORGANISM: Pasteurella multocida

<400> SEQUENCE: 9

Met Lys Ile Ala Lys Asn Val Val Ser Ile Ala Tyr Gln Val Arg
1               5                   10                  15

Thr Glu Asp Gly Val Leu Val Asp Glu Ala Pro Val Asn Gln Pro Leu
            20                  25                  30

Glu Tyr Leu Gln Gly His Asn Asn Leu Val Ile Gly Leu Glu Asn Ala
        35                  40                  45

Leu Glu Gly Lys Ala Val Gly Asp Lys Phe Glu Val Arg Val Lys Pro
    50                  55                  60

Glu Glu Ala Tyr Gly Glu Tyr Asn Glu Asn Met Val Gln Arg Val Pro
65                  70                  75                  80

Lys Asp Val Phe Gln Gly Val Asp Glu Leu Val Val Gly Met Arg Phe
                85                  90                  95

Ile Ala Asp Thr Asp Ile Gly Pro Leu Pro Val Ile Thr Glu Val
            100                 105                 110

Ala Glu Asn Asp Val Val Val Asp Gly Asn His Met Leu Ala Gly Gln
        115                 120                 125

Glu Leu Leu Phe Ser Val Glu Val Val Ala Thr Arg Glu Ala Thr Leu
    130                 135                 140

Glu Glu Ile Ala His Gly His Ile His Gln Gly Gly Cys Cys Gly
145                 150                 155                 160

Gly His His His Asp Ser Asp Glu Glu Gly His Gly Cys Gly Cys Gly
                165                 170                 175

Ser His His His Glu His Glu His His Ala His Asp Gly Cys Cys
            180                 185                 190

Gly Asn Gly Gly Cys Lys His
        195

<210> SEQ ID NO 10
<211> LENGTH: 156
<212> TYPE: PRT
<213> ORGANISM: Pasteurella multocida

<400> SEQUENCE: 10

Met Lys Ile Ala Lys Asn Val Val Ser Ile Ala Tyr Gln Val Arg
1               5                   10                  15

Thr Glu Asp Gly Val Leu Val Asp Glu Ala Pro Val Asn Gln Pro Leu
            20                  25                  30

Glu Tyr Leu Gln Gly His Asn Asn Leu Val Ile Gly Leu Glu Asn Ala
        35                  40                  45

Leu Glu Gly Lys Ala Val Gly Asp Lys Phe Glu Val Arg Val Lys Pro
    50                  55                  60

Glu Glu Ala Tyr Gly Glu Tyr Asn Glu Asn Met Val Gln Arg Val Pro
65                  70                  75                  80

Lys Asp Val Phe Gln Gly Val Asp Glu Leu Val Val Gly Met Arg Phe
                85                  90                  95
```

```
Ile Ala Asp Thr Asp Ile Gly Pro Leu Pro Val Val Ile Thr Glu Val
                100                 105                 110

Ala Glu Asn Asp Val Val Val Asp Gly Asn His Met Leu Ala Gly Gln
            115                 120                 125

Glu Leu Leu Phe Ser Val Glu Val Ala Thr Arg Glu Ala Thr Leu
        130                 135                 140

Glu Glu Ile Ala His Gly His Ile His Gln Glu Gly
145                 150                 155

<210> SEQ ID NO 11
<211> LENGTH: 270
<212> TYPE: PRT
<213> ORGANISM: Artificial Sequence
<220> FEATURE:
<223> OTHER INFORMATION: E. coli FkpA

<400> SEQUENCE: 11

Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Ala Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
    195                 200                 205

Ile Lys Lys Gly Gly Lys Ile Lys Leu Val Ile Pro Pro Glu Leu Ala
210                 215                 220

Tyr Gly Lys Ala Gly Val Pro Gly Ile Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270

<210> SEQ ID NO 12
<211> LENGTH: 245
<212> TYPE: PRT
<213> ORGANISM: Artificial Sequence
```

-continued

```
<220> FEATURE:
<223> OTHER INFORMATION: E. coli FkpA

<400> SEQUENCE: 12

Ala Glu Ala Ala Lys Pro Ala Thr Ala Ala Asp Ser Lys Ala Ala Phe
1               5                   10                  15

Lys Asn Asp Asp Gln Lys Ser Ala Tyr Ala Leu Gly Ala Ser Leu Gly
            20                  25                  30

Arg Tyr Met Glu Asn Ser Leu Lys Glu Gln Glu Lys Leu Gly Ile Lys
        35                  40                  45

Leu Asp Lys Asp Gln Leu Ile Ala Gly Val Gln Asp Ala Phe Ala Asp
    50                  55                  60

Lys Ser Lys Leu Ser Asp Gln Glu Ile Glu Gln Thr Leu Gln Ala Phe
65                  70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
            100                 105                 110

Glu Lys Gly Val Lys Thr Ser Thr Gly Leu Val Tyr Gln Val Val
        115                 120                 125

Glu Ala Gly Lys Gly Glu Ala Pro Lys Asp Ser Asp Thr Val Val Val
    130                 135                 140

Asn Tyr Lys Gly Thr Leu Ile Asp Gly Lys Glu Phe Asp Asn Ser Tyr
145                 150                 155                 160

Thr Arg Gly Glu Pro Leu Ser Phe Arg Leu Asp Gly Val Ile Pro Gly
                165                 170                 175

Trp Thr Glu Gly Leu Lys Asn Ile Lys Lys Gly Gly Lys Ile Lys Leu
            180                 185                 190

Val Ile Pro Pro Glu Leu Ala Tyr Gly Lys Ala Gly Val Pro Gly Ile
        195                 200                 205

Pro Pro Asn Ser Thr Leu Val Phe Asp Val Glu Leu Leu Asp Val Lys
    210                 215                 220

Pro Ala Pro Lys Ala Asp Ala Lys Pro Glu Ala Asp Ala Lys Ala Ala
225                 230                 235                 240

Asp Ser Ala Lys Lys
                245

<210> SEQ ID NO 13
<211> LENGTH: 241
<212> TYPE: PRT
<213> ORGANISM: Artificial Sequence
<220> FEATURE:
<223> OTHER INFORMATION: Epstein-Barr Virus nuclear antigen 1

<400> SEQUENCE: 13

Gly Arg Arg Pro Phe Phe His Pro Val Gly Glu Ala Asp Tyr Phe Glu
1               5                   10                  15

Tyr His Gln Glu Gly Gly Pro Asp Gly Glu Pro Asp Val Pro Pro Gly
            20                  25                  30

Ala Ile Glu Gln Gly Pro Ala Asp Asp Pro Gly Glu Gly Pro Ser Thr
        35                  40                  45

Gly Pro Arg Gly Gln Gly Asp Gly Gly Arg Arg Lys Lys Gly Gly Trp
    50                  55                  60
```

```
Phe Gly Lys His Arg Gly Gln Gly Gly Ser Asn Pro Lys Phe Glu Asn
 65                  70                  75                  80

Ile Ala Glu Gly Leu Arg Ala Leu Leu Ala Arg Ser His Val Glu Arg
                 85                  90                  95

Thr Thr Asp Glu Gly Thr Trp Val Ala Gly Val Phe Val Tyr Gly Gly
            100                 105                 110

Ser Lys Thr Ser Leu Tyr Asn Leu Arg Arg Gly Thr Ala Leu Ala Ile
        115                 120                 125

Pro Gln Ala Arg Leu Thr Pro Leu Ser Arg Leu Pro Phe Gly Met Ala
    130                 135                 140

Pro Gly Pro Gly Pro Gln Pro Gly Pro Leu Arg Glu Ser Ile Val Ala
145                 150                 155                 160

Tyr Phe Met Val Phe Leu Gln Thr His Ile Phe Ala Glu Val Leu Lys
                165                 170                 175

Asp Ala Ile Lys Asp Leu Val Met Thr Lys Pro Ala Pro Thr Ala Asn
                180                 185                 190

Ile Arg Val Thr Val Ala Ser Phe Asp Asp Gly Val Asp Leu Pro Pro
                195                 200                 205

Trp Phe Pro Pro Met Val Glu Gly Ala Ala Glu Gly Asp Asp Gly
    210                 215                 220

Asp Asp Gly Asp Glu Gly Gly Asp Gly Asp Glu Gly Glu Glu Gly Gln
225                 230                 235                 240

Glu

<210> SEQ ID NO 14
<211> LENGTH: 176
<212> TYPE: PRT
<213> ORGANISM: Artificial Sequence
<220> FEATURE:
<223> OTHER INFORMATION: Epstein-Barr Virus protein p18

<400> SEQUENCE: 14

Met Ala Arg Arg Leu Pro Lys Pro Thr Leu Gln Gly Arg Leu Glu Ala
  1               5                  10                  15

Asp Phe Pro Asp Ser Pro Leu Leu Pro Lys Phe Gln Glu Leu Asn Gln
                 20                  25                  30

Asn Asn Leu Pro Asn Asp Val Phe Arg Glu Ala Gln Arg Ser Tyr Leu
             35                  40                  45

Val Phe Leu Thr Ser Gln Phe Ala Tyr Glu Glu Tyr Val Gln Arg Thr
         50                  55                  60

Phe Gly Val Pro Arg Arg Gln Arg Ala Ile Asp Lys Arg Gln Arg Ala
 65                  70                  75                  80

Ser Val Ala Gly Ala Gly Ala His Ala His Leu Gly Gly Ser Ser Ala
                 85                  90                  95

Thr Pro Val Gln Gln Ala Gln Ala Ala Ala Ser Ala Gly Thr Gly Ala
            100                 105                 110

Leu Ala Ser Ser Ala Pro Ser Thr Ala Val Ala Gln Ser Ala Thr Pro
        115                 120                 125

Ser Val Ser Ser Ser Ile Ser Ser Leu Arg Ala Ala Thr Ser Gly Ala
    130                 135                 140

Thr Ala Ala Ala Ser Ala Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175
```

```
<210> SEQ ID NO 15
<211> LENGTH: 72
<212> TYPE: PRT
<213> ORGANISM: Artificial Sequence
<220> FEATURE:
<223> OTHER INFORMATION: Epstein-Barr Virus protein p18

<400> SEQUENCE: 15

Ala Ala Ser Ala Gly Thr Gly Ala Leu Ala Ser Ser Ala Pro Ser Thr
1               5                   10                  15

Ala Val Ala Gln Ser Ala Thr Pro Ser Val Ser Ser Ile Ser Ser
            20                  25                  30

Leu Arg Ala Ala Thr Ser Gly Ala Thr Ala Ala Ser Ala Ala Ala
        35                  40                  45

Ala Val Asp Thr Gly Ser Gly Gly Gly Gln Pro His Asp Thr Ala
    50                  55                  60

Pro Arg Gly Ala Arg Lys Lys Gln
65                  70

<210> SEQ ID NO 16
<211> LENGTH: 162
<212> TYPE: PRT
<213> ORGANISM: Artificial Sequence
<220> FEATURE:
<223> OTHER INFORMATION: Epstein-Barr Virus protein p23

<400> SEQUENCE: 16

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Ala Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp

<210> SEQ ID NO 17
<211> LENGTH: 23
<212> TYPE: PRT
<213> ORGANISM: Artificial Sequence
<220> FEATURE:
<223> OTHER INFORMATION: Linker sequence for cloing of expression
      cassettes
```

```
<400> SEQUENCE: 17

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 18
<211> LENGTH: 6
<212> TYPE: PRT
<213> ORGANISM: Artificial Sequence
<220> FEATURE:
<223> OTHER INFORMATION: hexa-histidine tag

<400> SEQUENCE: 18

His His His His His His
1               5
```